United States Patent
Brown et al.

(10) Patent No.: US 6,313,286 B1
(45) Date of Patent: Nov. 6, 2001

(54) NUCLEOSIDE ANALOGUES

(75) Inventors: Daniel Brown, Cambridge; Alan Hamilton, Amersham; David Loakes, Letchworth; Adrian Simmonds, Amersham; Clifford Smith, Tring, all of (GB)

(73) Assignee: Amersham Pharmacia Biotech UK Limited, Buckinghamshire (GB)

( * ) Notice: Subject to any disclaimer, the term of this patent is extended or adjusted under 35 U.S.C. 154(b) by 0 days.

(21) Appl. No.: 09/117,494

(22) PCT Filed: Feb. 3, 1997

(86) PCT No.: PCT/GB97/00312

§ 371 Date: Feb. 5, 1999

§ 102(e) Date: Feb. 5, 1999

(87) PCT Pub. No.: WO97/28177

PCT Pub. Date: Aug. 7, 1997

(30) Foreign Application Priority Data

Feb. 1, 1996 (GB) .................................................. 9602025

(51) Int. Cl.[7] .............................. C07H 19/00; C07H 19/22
(52) U.S. Cl. ...................... 536/27.1; 536/22.1; 536/23.1; 536/27.11; 536/27.13; 536/27.2; 435/6
(58) Field of Search ................................... 536/22.1, 23.1, 536/27.1, 27.11, 27.13, 27.2; 435/6

(56) References Cited

U.S. PATENT DOCUMENTS 4,965,350 * 10/1990 Inoue et al. .......................... 536/22.1
5,866,700 * 2/1999 Pfleiderer ............................. 536/25.3

FOREIGN PATENT DOCUMENTS 0 235 301    9/1987  (EP) .............................. C07H/19/04
WO 95/15395  6/1995  (WO) ............................. C12F/19/30

OTHER PUBLICATIONS

Fontanel et al., "P Labelling of Nonnucleosidic Maeties 5'—Attached to Oligonucleotides," *Analytical Biochemistry*, 214:338–340 (1993).
Basha, F.Z. et al., "A Novel Carbon–Animo Grignard Reagent: Its Use Use In An Efficient Pyrrolidine Synthesis," *Tetrahedron Lett.*, 25:5271–5274 (1984).
Dreyer, G.B. et al., "Sequence–Specific cleavage of single–stranded DNA: Oligodeoxynucleotide–EDTA–Fe(II)," *Proc. Natl. Acad. Sci.*, USA, 82:968–972 (1985).
Durland, R.H. et al., "Selective binding of Pyrido(2,3–d) pyrimidine 2'–Deoxyribonucleoside to AT Base Pairs in Antiparallel Triple Helices," *Bioconjugate Chemistry*, 6(3):278–282 (May, 1995).
Inoue, H. et al., "Synthesis and hybridization of dodecadeoxyribonucleotides containing a deoxynucleoside," *Nucleic Acids Research*, 13(19):7119–7128 (Oct. 11, 1985).
Hronowski et al., "Synthesis of New Carbocyclic Analogues of S'–Azido– and 3'–Amino–2', 3'–dideoxynucleosides," *J. Chem. Soc. Chem. Commun.* pp. 1547–1548 (1990).
Herdewijn et al., "Synthesis and Anti–HIV Activity of Different Sugar–Modified Pyrimidine and Purine Nucleosides," *J. Med. Chem.*, 31:2040–2048 (1988).
Griengl et al., 5–(Haloalkyl)–2'deoxyuridines; A Novel Type of Potent Antiviral Nucleoside Analogue, *J. Med. Chem.*, 28:1679–1684 (1985).
Lin, P.K.T. et al., "Synthesis and Duplex Stability of Oliogonucleotides Containing Cytoline–Thymine Analogues," *Nucleic Acids Research*, 17:10373–10383 (1989).
Lin, P.K.T. et al., "Oliogonucleotides Containing Degenerate Bases," *Methods in Molecular Biology*, vol. 26, pp. 187–206, Agrawal, S. (Ed.) Humana Press, Inc. (1994).
Loakes, D. et al., "Antiviral Activity of bicyclic pyrimidine nucleosides," *Antiviral Chemistry and Chemotherapy*, 6(6):371–378 (1995).
Nedderman, A.N.R. et al., "Molecular basis for methoxyamine–initiated mutagenesis: 1H nuclear magnetic resonance studies of oligonucleotide duplexes containing base–modified cytosine residues," *Journal of Molecular Biology*, 230(3):1068–1076 (Apr. 5, 1993).
Lin, P.K.T., et al., "Synthesis of Oligodeoxyribonucleotides Containing Degenerated Bases and Their Use As Primers in the Polymerase Chain Reaction," *Nucleic Acids Research*, 20(19):5149–5142 (1992).
Ruth, J.L. et al., "C–5 Substituted Pyrimidine Nucleosides. 1. Synthesis of C–5 Allyl, Propyl, and Propenyl Uracil and Cytosine Nucleosides via Organopalladium Intermediates," *J. Org. Chem.*, 43:2870–2876 (1978).

* cited by examiner

Primary Examiner—James O. Wilson
(74) Attorney, Agent, or Firm—Marshall, Gerstein, & Borun

(57) ABSTRACT

Nucleoside analogues containing the degenerate base analogue P and derivatives thereof are provided with reporter moieties preferably comprising signal moieties. The nucleoside analogues are useful for labeling DNA or RNA or for incorporating in oligonucleotides.

11 Claims, No Drawings

NUCLEOSIDE ANALOGUES

CROSS REFERENCE TO RELATED APPLICATIONS

This is the national phase of PCT/GB97/00312 filed Feb. 3, 1997 which was based upon Great Britain application Ser. No. GB 9602025.0 filed Feb. 1, 1996.

Nucleic acids are manipulated in vitro in a wide variety of research and diagnostic techniques. The methods can involve the synthesis of nucleic acid probes by means of polymerase or terminal transferase enzymes for the purposes of labelling or determination of base sequence identity. Labelling often involves the incorporation of a nucleotide which is chemically labelled or which is of a particular chemical composition so as to make it detectable. Nucleic acid probes made in this way can be used to determine the presence of a nucleic acid target which has a complementary sequence by means of hybridisation of the probe to the target.

Another method for introducing chemically labelled or otherwise modified nucleotides into DNA involves chemical synthesis using nucleoside phosphoramidite or other precursors which are linked together in any desired sequence in oligonucleotide synthesisers, the final product being indistinguishable from DNA made by the use of polymerases.

In certain situations it is useful to be able to incorporate a base analogue into an oligo- or poly-nucleotide which does not have the base pairing specificity of the natural bases. This invention describes new nucleoside analogues which are capable of forming base pairs with more than one nucleotide, and which carry a reporter group.

P Kong Thoo Lin and D M Brown reported (Nucleic Acids Research, 1989, Vol 17, pages 10373–10383) the synthesis of a monomer containing the degenerate base analogue P, (6H, 8H-3-4-dihydropyrimido[4,5-c][1.2] oxazin-7-one). Due to the ability of this base analogue to exist in amino and imino tautomers, it can base pair with both purine bases A and G. The authors found that oligomers containing one or more P bases formed DNA duplexes of comparable stability to the parent duplexes and which also showed sharp transitions on melting. Further evidence confirmed that the base pairs P/A and P/G were essentially of the Watson-Crick type.

The authors also discussed the potential use of this base analogue in hybridisation probes and primers, when the base can be put at positions of degeneracy thus both avoiding the need for multiple-chain primers (or probes) and significantly reducing the chain multiplicity. Indeed oligonucleotides containing several P bases were effective in dot blot hybridisation and DNA sequencing experiments.

In Nucleic Acids Research, 1992, Vol 20, No 19, pages 5149–5152, these authors also demonstrated the use of oligonucleotides containing the P base at the 3'-end and elsewhere as primers in polymerase chain reaction (PCR) experiments.

EP 0 235 301 describes pyridopyrimidine nucleotide derivatives which can form base pairs with guanine or adenine, and which are fluorescent in their own right. Excitation of, these derivatives is in the UV region (330–350 nm)

Purine and pyrimidine base nucleosides and nucleotides have been derivatised with reporter groups and are well known and widely used for labelling DNA or RNA and in other molecular biology applications. But these molecules are capable of base-pairing only with one of A, C, G and T and the nucleoside triphosphates are often poor enzyme substrates. There is a need for a nucleoside analogue whose triphosphate is a good enzyme substrate and which has a base analogue that is degenerate, by having the ability to base pair with two or three of the natural bases e.g. with both pyrimidines (T/C) or both purines (A/G), or universal, by forming base-pairs with each of the natural bases without discrimination. This invention makes use of the P base to address these needs.

The invention provides a nucleoside analogue of the formula

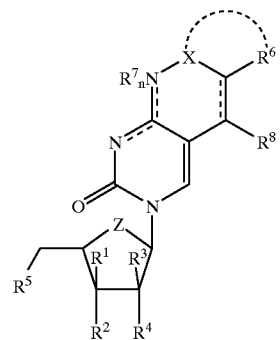

X is O, S, Se, SO, CO or N—$R^{10}$, the curved dotted line represents an optional link between $R^6$ and $R^{10}$, $R^1$, $R^2$, $R^3$ and $R^4$ are the same or different and each is H, OH, F, $NH_2$, $N_3$, O-hydrocarbyl, or a reporter moiety, $R^5$ is OH or mono-, di- or tri-phosphate or -thiophosphate or corresponding boranophosphate, or one of $R^2$ and $R^5$ is a phosphoramidite or other group for incorporation in a polynucleotide chain, Z is O, S, Se, SO, $NR^9$ or $CH_2$, and $R^6$, $R^7$, $R^8$, $R^9$ and $R^{10}$ are the same or different and each is H or alkyl or aryl or a reporter moiety, n is 0 or 1, provided that at least one reporter moiety is present, wherein a reporter moiety comprises a linker group, together with a signal moiety or a solid surface or a reactive group by which a signal moiety or a solid surface may be attached to the nucleoside analogue.

A nucleoside analogue is a molecule which is capable of being incorporated, either chemically or enzymatically, into an oligomeric or polymeric nucleic acid (DNA or RNA) chain, and when so incorporated of forming a base pair with a nucleotide in a complementary chain or base stacking in the appropriate nucleic acid chain.

A reporter moiety may be any one of various things. It may be a radioisotope by means of which the nucleoside analogue is rendered easily detectable, for example 32-P or 33-P or 35-S incorporated in a phosphate or thiophosphate or phosphoramidite or H-phosphonate group, or alternatively 3-H or 125-I. It may be a stable isotope detectable by mass spectrometry. It may be a signal moiety e.g. an enzyme, hapten, fluorophore, chemiluminescent group, Raman label or electrochemical label. The reporter moiety may comprise a signal moiety and a linker group joining it to the remainder of the molecule, which linker group may be a chain of up to 30 carbon, nitrogen, oxygen and sulphur atoms, rigid or flexible, unsaturated or saturated as well known in the field. The reporter moiety may comprise a solid surface and a linker group joining it to the rest of the molecule. The reporter moiety may consist of a linker group with a terminal or other reactive group, e.g. $NH_2$, OH, COOH, $CONH_2$ or SH, by which a signal moiety and/or a solid surface may be attached, before or after incorporation of the nucleoside analogue in a nucleic acid chain. Such reporter groups are well known and well described in the literature.

$R^1$, $R^2$, $R^3$ and $R^4$ may each be H, OH, F, $NH_2$, $N_3$, O-alkyl or a reporter moiety. Thus ribonucleosides, and deoxyribonucleosides and dideoxyribonucleosides are envisaged together with other nucleoside analogues. These sugar substituents may contain a reporter moiety in addition to the one or two present in the base.

$R^5$ is OH or mono-, di- or tri-phosphate or -thiophosphate or corresponding boranophosphate. Alternatively, one of $R^2$ and $R^5$ may be a phosphoramidite or H-phosphonate or methylphosphonate or phosphorothioate or an appropriate linkage to a solid surface e.g. hemisuccinate controlled pore glass, or other group for incorporation, generally by chemical means, in a polynucleotide chain. The use of phosphoramidites and related derivatives in synthesising ofigonucleotides is well known and described in the literature. From nucleosides ($R^5$ is OH) it is readily possible to make the corresponding nucleotides ($R^5$ is triphosphate) by literature methods.

In the new nucleoside analogues to which this invention is directed, at least one reporter moiety is present preferably in the base analogue or in the sugar moiety or a phosphate group. Reporter moieties may be introduced into the sugar moiety of a nucleoside analogue by literature methods (e.g J. Chem. Soc. Chem. Commun. 1990, 1547–8; J. Med. Chem., 1988, 31. 2040–8). Reporters in the form of isotopic labels may be introduced into phosphate groups by literature methods (Analytical Biochemistry, 214, 338–340, 1993; WO 95/15395).

The base analogue with which this invention is concerned is a fused ring structure in which one ring contains an optional double bond shown in the diagram as a dashed line. When a double bond is present, the ring is flat and no chirality problem arises. When a single bond is present, the introduction of a reporter moiety $R^6$ or $R^8$ creates a chiral centre. It may be helpful if the chirality is chosen so that the reporter sticks out of, and not back into, the nucleic acid helix.

The nucleoside analogues of this invention are useful for labelling DNA or RNA or for incorporating in oligonucleotides, with the advantage over conventional hapten labelled nucleotides such as fluorescein-dUTP of being able to replace more than one base or more efficient enzymatic incorporation. A reporter moiety is attached at a position so as not to interfere with the physical or biochemical properties of the nucleoside analogue, in particular its ability to be incorporated in single stranded and double stranded nucleic acids without significantly reducing the Tm. A template containing the incorporated nucleoside analogue of this invention is suitable for copying in nucleic acid synthesis. If a reporter moiety of the incorporated nucleoside analogue consists of a linker group, then a signal moiety can be introduced into the incorporated nucleoside analogue by being attached through a terminal reactive group of the linker group.

In the nucleoside analogue described above, a deoxy or dideoxy or other substituted ribose moiety is linked at the 1'-position to a base analogue. This base analogue is preferably capable of acting as a hapten so as to bind an antibody and of doing this whether or not a reporter moiety is present. In another aspect the invention provides a method of detecting a nucleoside analogue, as described herein but in which a reporter moiety may or may not be present, said nucleoside analogue being incorporated in a single stranded or double stranded nucleic acid chain, which method comprises using for detection an antibody which binds to the base analogue thereof.

In primer walking sequencing, a primer/template complex is extended with a polymerase and chain terminated to generate a nested set of fragments where the sequence is read after electrophoresis and detection (radioactive or fluorescent). A second primer is then synthesised using the sequence information near to the end of the sequence obtained from the first primer. This second ("walking") primer is then used for sequencing the same template. Primer walking sequencing is more efficient in terms of generating less redundant sequence information than the alternative "shot gun" approach.

The main disadvantage with primer walking is the need to synthesise a walking primer after each round of sequencing. Cycle sequencing requires primers that have annealing temperatures near to the optimal temperature for the polymerase used for the cycle sequencing. Primers between 18 and 24 residues long are generally used for cycle sequencing. The size of a presynthesised walking primer set required has made primer walking cycle sequencing an impractical proposition. The use of nucleoside analogues that are degenerate or universal addresses this problem. The use of such analogues that are also labelled, e.g. the nucleoside analogues of this invention will also help to overcome the problem. Preferred reporter moieties for this purpose are radioactive isotopes or fluorescent groups, such as are used in conventional cycle sequencing reactions.

The nucleoside analogues of this invention can also be used in any of the existing applications which use native nucleic acid probes labelled with haptens or fluorophores, or other reporter groups, for example on Southern blots, dot blots and in polyacrylamide or agarose gel based methods. The probes may be detected with antibodies targeted either against haptens which are attached to the base analogues or against the base analogues themselves which would be advantageous in avoiding additional chemical modification. Antibodies used in this way are normally labelled with a detectable group such as a fluorophore or an enzyme. Fluorescent detection may also be used if the base analogue itself is fluorescent or if there is a fluorophore attached to the nucleoside analogue.

The nucleoside analogues of the present invention with the combination of molecular diversity and increased numbers of positions where reporter groups may be added can result in a series of improved enzyme substrates.

The nucleoside analogue of the present invention in its imino and amino tautomeric form pairing with adenine and guanine is shown below. In each case $C_1$ represents a deoxy or dideoxy or other substituted ribose moiety.

P-imino: A

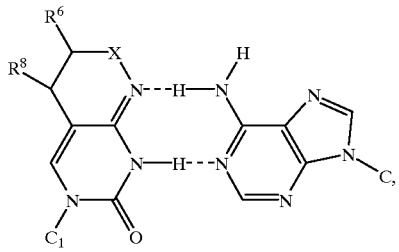

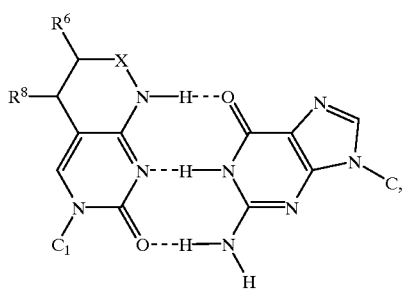

DETAILED DESCRIPTION OF THE INVENTION

5-Allyl-2'-deoxyuridine is the initial building block for the synthesis of the range of P base analogues (X=O) described in the following examples. The synthesis of 5-allyl-2'-deoxyuridine is described by J. L. Ruth and D. E. Bergstrom *J. Org. Chem.* 43, 2870–2876 (1978) along with the corresponding 5-allyl-uridine derivative. To those skilled in the art of chemical synthesis it is obvious that, by using suitable protecting groups on the 5-allyl-uridine ribose sugar, related ribose derivatives of example compounds (2.4), (3.6), (3.7),(4.4) and their related triphosphate derivatives can be readily synthesised. Such a protecting group could be tert-butyldimethylsilane thus maintaining the same silyl protecting group strategy used throughout the described synthesis. In example 6 there are described methods for the generation of a protected 5-(2-chloroethyl)-uridine that could be used to provide ribose derivative analogues of example compounds (6.4), (7.3), (7.4) and (8.5).

Similarly, to one skilled in the art of chemical synthesis, it is obvious that ribo or deoxy ribo compounds described within the following examples could easily be converted to the dideoxy derivatives by known methods.

EXAMPLE 1

Synthesis of 3',5'-O-(1,3-(1,1,3,3-tetraisopropyidisiloxanylidene))-5-(carbonylmethyl)-2'-deoxyuridine (1,3) and 3',5'-O-(1l,3-(1,3,3-tetraisopropyldisiloxanylidene))-5-(2,3-epoxypropyl)-2'-deoxyuridine (1,4)

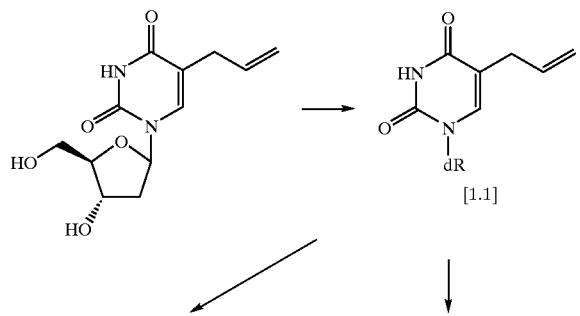

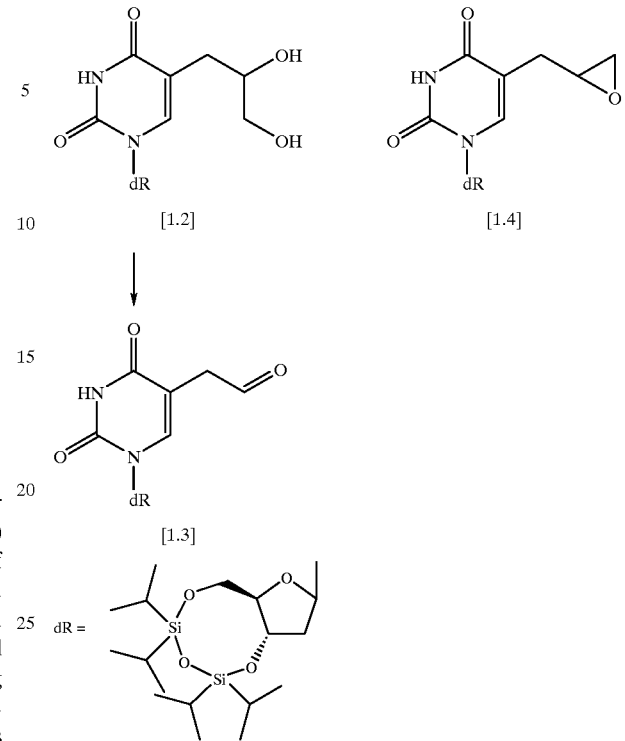

Preparation of 3',5'-O-(1,3-(1,1,3,3-tetraisopropyidisiloxanylidene))-5-(2-propenyl)-2'-deoxyuridine (1.1)

5-Allyl-2'-deoxyuridine was prepared according to literature procedures; G. B. Dreyer & P. B. Dervan, *Proc. Natl. Acad. Sci. USA*, 82, 968–972, (1985); J. L. Ruth & D. E. Bergstrom, *J. Org. Chem.*, 43, 2870, (1978).

5-Allyl-2'-deoxyuridine (11.3 g, 42mmol) was first dried by twice dissolving in dry pyridine and evaporating to dryness under reduced pressure. The resulting foam was redissolved in dry pyridine (50ml), placed under nitrogen atmosphere and cooled to 0° C. in an ice-water bath. To this solution was added 1,3-dichloro-1,1,3,3-tetraisopropyldisiloxane (12.6 g, 42 mmol), via syringe over 5 minutes. The resulting mixture was stirred for 16 hours at room temperature, then the solvent was removed by evaporation under reduced pressure. The residue was partitioned between ethyl acetate and water; the organic layer was retained, washed with water and brine, then dried ($Na_2SO_4$), filtered and evaporated under reduced pressure to a sticky solid. This was purified by flash column chromatography (silica; ethyl acetate 50%: light petroleum 50%) to give the title compound (1.1) 14.5 g (68%). Mpt. 168° C.; UV ($CHCl_3$) 268 nm. $\delta_H$(300 MHz; $CDCl_3$) 0.85–1.05 (28H, m, Si—iPr×4), 2.18–2.48 (2H, m, sugar 2'), 3.02 (2H, m, —C$\underline{H}_2$—CH=$CH_2$), 3.72 (1H, m, sugar 4'), 3.99 (2H, m, sugar 5'), 4.45 (1H, m, sugar 3'), 5.78 (1H, m, 5.06 (2H, m, —$CH_2$—C$\underline{H}$=$CH_2$), 5.78 (1H, m, —$CH_2$—C$\underline{H}$=$CH_2$), 6.02 (1H, m, sugar 1'), 7.24 (1H, s, C6), 8.44 (1H, s, N3) ppm Preparation of 3',5'-O-(1,3-(1,1,3,3-tetraisopropyidisiloxanylidene))-5-(2(R,S),3-dihydroxypropyl)-2'-deoxyuridine (1.2)

3',5'-O-(1,3-(1,1,3,3-tetraisopropyldisiloxanylidene))-5-(2-propenyl)-2'-deoxyuridine (1.1) (7.0 g, 13.7mmol) and N-methylmorpholine-N-oxide (4.79. 40 mmol) were dissolved in acetone (200 ml). To this solution was added a solution of potassium osmate dihydrate (50 mg) in water (10 ml), dropwise over 5 minutes. The resulting mixture was stirred at room temperature for 16 hours, then the solvent was removed by evaporation. The residue was partitioned between diethyl ether and water; the organic layer was retained, washed with water and brine, then dried ($Na_2SO_4$), filtered and evaporated under reduced pressure. The residue was purified by flash column chromatography (silica; 5–15% methanol/dichloromethane) to give the title compound (1.2) as a white foam, 5.4 g (72%). UV ($CHCl_3$) 270 nm.

$\delta_H$(300 MHz; $CDCl_3$) 0.89–1.06 (28H, m, Si—iPr×4), 1.5–2.0 (1H, broad, OH), 2.14–2.57 (4H, m, sugar 2'+—C$\underline{H}_2$—CHOH—$CH_2OH$), 3.47–3.80 (5H, m, sugar 4'+$CH_2$—C$\underline{H}$OH—$CH_2OH$ +OH), 3.97–4.09 (2H, m, sugar 5'), 4.46 (1H, m, sugar 3'), 6.04 (1H, m, sugar 1'), 7.44+7.47 (1H, 2s, C6 diastereomers), 9.0–9.4 (1H, broad, N3) ppm.

Preparation of 3',5'-O-(1,3-(1,1,3,3-tetraisopropyidisiloxanylidene))-5-(carbonylmethyl)-2'-deoxyuridine (1.3)

3', 5'-O-(1,3-(1,1,3,3-tetraisopropyldisiloxanylidene))-5-(2(R,S),3-dihydroxypropyl)-2'-deoxyuridine (2.18 g, 4.0 mmol) was dissolved in tetrahydrofuran (50 ml), then water (40 ml) added. To this solution was added a solution of sodium periodate (0.94 g, 4.4 mmol) in water (10 ml). This mixture was stirred at room temperature for 2 hours, then partitioned between diethyl ether and water. The organic layer was retained, washed with water and brine, then dried ($Na_2SO_4$), filtered and evaporated under reduced pressure. The residue was purified by flash column chromatography (silica; 4% methanol/dichloromethane) to give the title compound (1.3) as a white foam, 1.9 g (93%). Mpt. 187° C.; UV ($CHCl_3$) 268 nm.

$\delta_H$(300 MHz; $CDCl_3$+$CD_3CO_2D$) 0.8–1.1 (28H, m, Si—iPr×4), 2.24–2.54 (2H, m sugar 2'), 3.39 (2H, s, —C$\underline{H}$,—CHO), 3.76 (1H, m, sugar 4'), 4.05 (2H, m, sugar 5'), 4,45 (1H, m, sugar 3'), 6.02 (1H, m, sugar 1'), 7.56 (1H, s, C6), 8.46 (1H, s, N3), 9.70 (1H, s, $CH_2$—C$\underline{H}$O) ppm.

Preparation of 3',5'-O-(1,3-(1,1,3,3-tetraisopropyidisiloxanylidene))-5-(2,3-epoxypropyl)-2'-deoxyuridine (1.4)

3',5'-O-(1,3-(1,1,3,3-tetraisopropyldisiloxanylidene))-5-(2-propenyl)-2'-deoxyuridine (1.1) (2.04 g, 4.0 mmol) was dissolved in dichloromethane (25 ml); to this solution was then added 3-chloroperoxybenzoic acid, 55% (1.3 g=4.1 mmol mCPBA). This mixture was stirred at room temperature for 16 hours. It was then washed three times with 10% aqueous sodium carbonate solution, then brine. It was dried ($Na_2SO_4$), filtered and evaporated under reduced pressure to give a solid, which was purified by flash column chromatography (silica; 25% ethyl acetate/dichloromethane) to give the title compounds (1.4), 1.25 g (59%). UV (MeOH) 266 nm.

$\delta_H$(300 MHz; $CDCl_3$) 0.96–1.08 (28H, m, Si—iPr×4), 2.30–2.52 (4H, m, sugar 2'+—C$\underline{H}_2$—CH(O)$CH_2$), 2.65–2.77 (2H, m, —$CH_2$—CH(O)C$\underline{H}_2$), 3.11 (1H, m, —$CH_2$—C$\underline{H}$(O)$CH_2$), 3.75 (1H, m, sugar 4'), 4.03 (2H, m, sugar 5'), 4.50 (1H, m, sugar 3'), 6.06 (1H, m, sugar 1'), 7.41+7.44 (1H, 2s, C6 diastereomers), 8.57 (1H, s, N3) ppm.

EXAMPLE 2

Synthesis of 6-(2-deoxy-β-D-ribofuranosyl)-3,4-dihydro-3(R,S)-methyl-8H-pyrimido[4,5-c][1,2]oxazin-7-one (2.4)

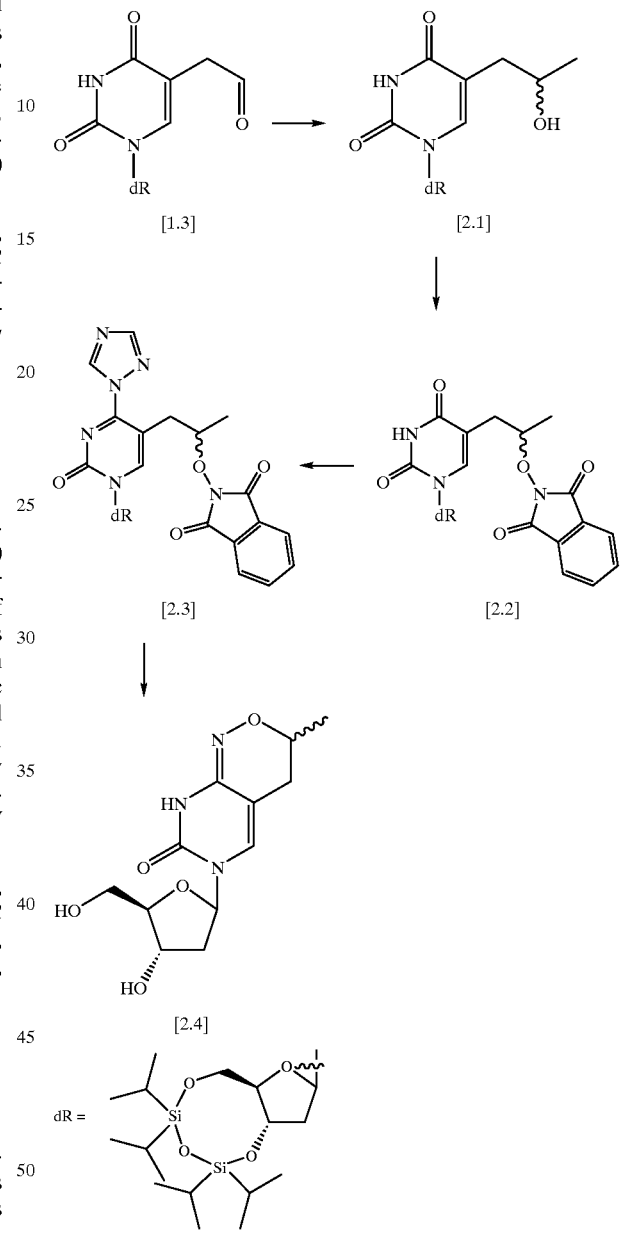

Preparation of 3',5'-O-(1,3-(1,1,3,3-tetraisopropyidisiloxanylidene))-5-(2(R,S)-hydroxypropyl)-2'-deoxyuridine (2.1)

To methyl magnesium bromide (35 ml of a 1.4M solution in ether, 49 mmol) at 0° C. under nitrogen was added by dropwise addition a mixture of 3',5'-O-(1,3-(1,1,3,3-tetraisopropyidisiloxanylidene))-5-(carbonylmethyl)-2'-deoxyuridine (1.3) and 3',5'-O-(1,3-(1,1,3,3-tetraisopropyidisiloxanylidene))-5-formyl-2'-deoxyuridine (3.95 g of a 3:1 mixture by proton NMR, approx 7 mmol*) and acetic acid (100 μl, 1.75 mmol) in dry ether (35 ml) over 15 minutes. The reaction mixture was left to stir at 0° C. under nitrogen for 30 minutes before being quenched by pouring into a saturated ammonium chloride solution (approx. 200 ml). The products were extracted with ethyl acetate and the organic phase washed with water, brine, 0.1M HCl and brine again to remove the bulk of the magnesium salts. The organic layer was removed under reduced pressure and the resulting residue subjected to a silica gel flash column purification using a methanol/dichloromethane 5:95 elution solvent. Yield 1.79 g of a gum consisting of the title compounds (2.1) and the corresponding 3',5'-O-(1,3-(1,1,3,3-tetraisopropyidisiloxanylidene)-5-(1(R,S)-hydroxyethyl)-2'-deoxyuridine. Ratio 2.2:1 by proton NMR. Rf 0.27 and 0.31 respectively in methanol/dichloromethane 5:95 on t.i.c.

Data for mixture of products: $\delta_H$($^{300}$ MHz; CDCl$_3$) 0.9–1.1 (28H, m, SiCH(CH$_3$)$_2$) 1.20–1.22 (3H, pair of d, diastereomic CH$_3$), 2.25–2.6 (4H, m, CH$_2$ 2' CH$_2$ 5), 3.8 (1H, m, H4'), 3.7–4.05 (3H, m, CHOH—CH$_3$ CH$_2$ 5'),4.5 (1H, m, H3'), 6.05 (1H,m, H1'), 7.41–7.46 (1H, pair of s, H6), 8.43 (1H, s, NH) ppm.

* NB The formyl species was formed by over-oxidation during the preparation of compound (1.3) and was not removed during the purification procedure. The corresponding 5-(1-R,S)-hydroxyethyl) has proton-NMR signals at $\delta$1.46–1.49 (pair of d, diastereomeric CH$_3$) 4.65 (m, CHOH—CH$_3$) 7.50–7.58 (pair of s, H6) ppm, as well as overlap with title compound signals.

Preparation of 3',5'-O-(1,3-(1,1,3,3-tetraisopropyldisiloxanylidene))-5-(2(R,S)-phthalimido-oxypropyl)-2'-deoxyuridine (2.2)

To 3',5'-O-( 1,3-(1,1,3,3-tetraisopropyldisiloxanylidene))-5-(2(R,S)-hydroxypropyl)-2'-deoxyuridine (2.1) mixed with the 1-(R,S)-hydroxyethyl analogue (1.79 g, approx. 3.4 mmol of (2.1)) in dry THF (40 ml) under nitrogen at room temperature was added triphenylphosphine (0.886 g, 3.4 mmol), N-hydroxyphthalimide (0.551 g, 3.4 mmol) and diethyl azodicarboxylate (0.58 ml, 3.7 mmol). There was a transient red coloration which faded to yellow. The reaction mixture was then left to stir at room temperature under nitrogen for 20 hours. The solvent was removed under reduced pressure and the resultant residue subjected to silica flash column chromatography using ether, light petroleum, dichloromethane 70:15:15 as eluant. Mixed fractions were combined and repurified again to provide title compounds (2.2) as a gum. Yield 1.07 g. Rf 0.47 and 0.55 on TLC eluant ether for the two diastereomers.

$\delta_H$(300 MHz; CDCl$_3$) 0.9–1.05 (28H, m, SiCH(CH$_3$)$_2$), 1.3–1.4 (3H, pair of d, diastereomeric CH$_3$), 2.4–2.75 (4H, m, =C—CH$_2$, CH$_2$2'), 3.75 (1H, m, H4'), 4.0 (2H, m, CH$_2$5') 4.2–4.6 (2H, m, H3' and NOC$\underline{H}$ diastereomeric pair), 6.1–6.25 (1H, pair of m, diasteromeric H1'), 7.65–7.82 (5H, m, ArH, H6), 8.22–8.25 (1H, pair of s, diastereomeric NH) ppm.

Preparation of 1-(3,5-O-(1,3-( 1,1,3,3-tetraisopropyidisiloxanylidene))-2-deoxy-β-D-ribofuranosyl)4-triazolo-5-(2(R,S)-phthalimido-oxypropyl)-1H-pyrimidin-2-one (2.3)

To 1,2,4-triazole (4.2 g, 60.7 mmol) dissolved in dry acetonitrile (30 ml) at 0° C. was added triethylamine (10.3 ml, 73.5 mmol) followed by dropwise addition of phosphorus oxychloride (1.15 ml. 12.4 mmol) dissolved in acetonitrile (10 ml) over 10 minutes. The mixture was allowed to stir at 0° C. under nitrogen for 10 minutes followed by 20 minutes at room temperature. To the reaction mixture was added dropwise, over 20 minutes, 3',5'-O-(1,3-(1,1,3,3-tetraisopropyldisiloxanylidene))-5-(2(R,S)-phthalimido-oxypropyl)-2'-deoxyuridine (2.2) (1.07 g) dissolved in dry acetonitrile (20 ml). The reaction mixture was stirred at room temperature for 50 minutes before removing the reaction solvent under reduced pressure. The residue was partitioned between dichloromethane and brine. The organic phase was separated off, dried with magnesium sulphate and concentrated to a gum under reduced pressure. Product purification was performed by silica gel flash chromatography using a gradient elution with ether, ether/ethyl acetate 1:1 and finally neat ethyl acetate to give the title compounds (2.3) as a gum. Yield 0.59 g. Rf 0.24 and 0.29 in ethyl acetate on silica TLC for the two diastereomers.

$\delta_H$(300 MHz; CDCl$_3$) 0.9–1.2 (28H, m, SiCH(CH$_3$)$_2$), 1.4–1.52 (3H, pair of d, diastereomeric CH$_3$), 2.5–3.0 (3H, m, sugar H2 and H2', 1H from =C—CH$_2$), 3.4–5.3 (6H, series of m, sugar H4,H3, 2×H5 and 1H from =C—CH$_2$, NOCH), 6.04–6.25 (1H, pair of m, diastereomeric=CH), 8.26–8.4 (1H, pair of s, diastereomeric triazole H), 9.3–9.35 (1H, pair of s, diastereomeric pair triazole H) ppm.

Preparation of 6-(2-deoxy-β-D-ribofuranosyl)-3,4-dihydro-3(R,S)-methyl-8H-pyrimido[4,5-c][1,2]oxazin-7-one (2.4)

1-(3,5-O-(1,3-(1,1,3,3-Tetraisopropyidisiloxanylidene))-2-deoxy-β-D-ribofuranosyl)-4-triazolo-5-(2(R,S)-phthalimido-oxypropyl)-1H-pyrimidin-2-one (2.3) (0.59 g, 0.81 mmol) was dissolved in dry dioxan saturated with ammonia (100 ml) and the solution stirred at room temperature for 18 hours. The dioxan was removed under reduced pressure and the cyclised product purified by silica gel flash chromatography using ether as eluant to give a colourless gum. Yield 310 mg. Rf 0.44 in ether on silica TLC; no diastereomeric separation was observed.

The sugar was deprotected in the following manner: To the product from above (208 mg, 0.4 mmol) dissolved in tetrahydrofuran (5 ml) was added tetra-n-butylammonium fluoride (435 μl of a 1.0 M solution in THF, 0.44 mmol) and the mixture was stirred for 5 minutes at room temperature. The solvent was removed under reduced pressure and the product purified by silica gel flash chromatography using methanol/ethyl acetate 1:9 to give the title compounds (2.4) as a clear gum. Yield 84 mg. Rf 0.33 in methanol/ethyl acetate 1:9 on silica TLC; no diastereomeric separation was observed.

67 $_H$(300 MHz;CD$_3$OD) 1.2 (3H, d, CH$_3$J 6.2 Hz), 2.04–2.08 (2H, m, CH$_2$-), 2.18–2.27 (1H, m, sugar H2), 2.52–2.57 (1H, m, sugar H2'), 3.6–3.75 (3H, m, sugar 2×H5 and C$\underline{H}$—CH$_3$), 3.75 (1H, m, sugar H4), 4.27 (1H, m, sugar H3), 6.15 (1H, m, sugar H1), 7.00 (1H, s, $\underline{H}$C=C) ppm.

The use of $^{14}$C methyl magnesium bromide in preparation on compound (2.1) renders the above synthesis a formal synthesis of a radioactive species.

EXAMPLE 3

Synthesis of 6-(2-deoxy-β-D-ribofuranosyl)-3,4-dihydro-3(R,S)-(N(2,4-dinitrophenylacyl)-3-aminopropyl)-8H-pyrimido[4,5-c][1,2]oxazin-7-one [3,6] and 6-(2-deoxy-β-D-ribofuranosyl)-3,4-dihydro-3(R,S)-(N-(6-(fluorescein-5-(and-6)-carboxamidohexanoyl))-3-aminopropyl)-8H-pyrimido[4,5-c][1,2]oxazin-7-one [3,7]

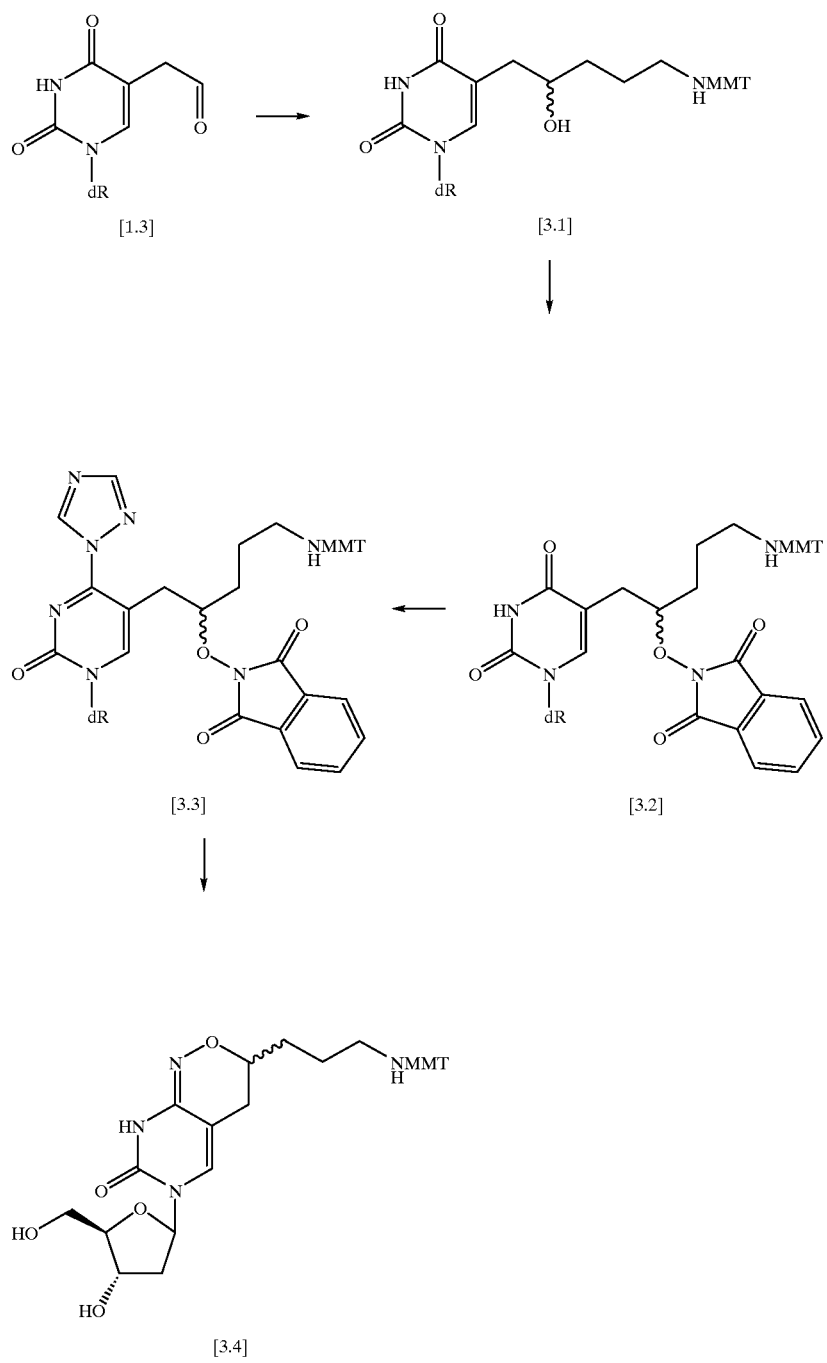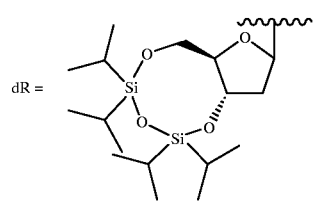

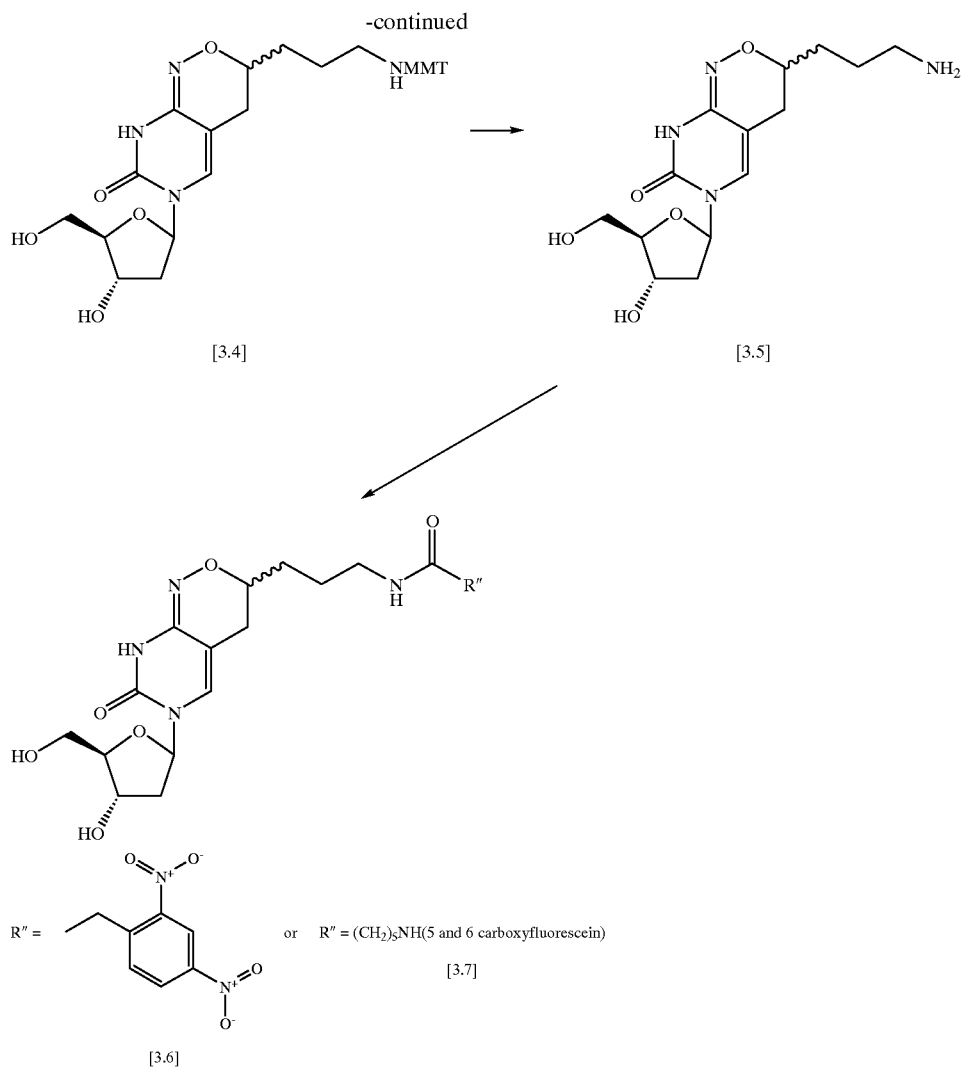

Preparation of 3',5'-O-(1,3-(1,1,3,3-tetraisopropyidisiloxanylidene))-5-(N-(4-methoxytriphenylmethyl)-5-amino-2(R,S)-hydroxypentyl)-2'-deoxyuridine (3.1)

To magnesium turnings (520 mgs, 217 mgram atom) in dry ether (20 ml) at room temperature under $N_2$ was added a crystal of iodine followed by a slow, dropwise addition of 2,2,5,5-tetramethyl-1-aza-2,5-disilacyclopentane-3-bromopropane (5.46 g, 27.3 mmol) in anhydrous ether (20 ml). The Grignard preparation was allowed to stir at room temperature under $N_2$ for a further 30 minutes after addition had been completed. To the now formed 2,2,5,5-tetramethyl-1-aza-2,5-disilacyclopentane-1-propylmagnesium bromide (Ref. below) was added, by slow dropwise addition over 15 minutes a solution of 3',5'-O-(1,3-(1,1,3,3-tetraisopropyldisiloxanylidene))-5-(2-carbonylmethyl)-2'-deoxyuridine compound (2.45 g, 4.79 mmol) and acetic acid (100 μl, 1.75 mmol) in anhydrous tetrahydrofuran (40 ml). The reaction mixture was permitted to stir for a further 30 minutes at room temperature under $N_2$ to ensure completion of the reaction. The reaction was quenched by pouring into a saturated $NH_4Cl$ solution (250 ml) and brine (100 ml) mixture. The organic solvent was removed under reduced pressure and the product subsequently extracted with dichloromethane (x3). The dichloromethane extracts were combined, dried with magnesium sulphate and concentrated under reduced pressure to a gum which was dried under high vacuum. The gum was dissolved in dichloromethane (20 ml) and 4-methoxytriphenylmethyl chloride (1.77 g, 5.75 mmol) and anhydrous triethylamine (3.3 ml, 23.95 mmol) were added. The reaction mixture was left to stir at room temperature for 18 hours. The organic solution was washed with brine (x1), dried over magnesium sulphate and finally concentrated under reduced pressure to a gum. Product purification was achieved by silica gel flash chromatography, eluant ether, to provide the title compound (3.1) as a pale yellow foam. Yield 2.45 g, 61%, Rf 0.41 in ether on silica t.l.c.

$δ_H$(300 MHz; $CDCl_3$) 0.95–1.0(28H, m, Si—C$\underline{H}$(C$\underline{H}_3$)$_2$), 1.4–1.6(4H, m, $CH_2CH_2$), 2.1–2.6(6H,m,$CH_2N$, =C—$CH_2$, H2,H2'), 3.7–$OCH_3$, H4, C$\underline{H}$—OH), 3.9–4.1(2H, m, H5), 4.5(1H, m, H3), 6.05(1H, m, H1), 6.8(2H, d, ArH), 7.15–7.46(15H, m, ArH, =CH) ppm.

Ref. F. Z. Basha and J. F. DeBernardis. *Tetrahedron Lett.* 25, 5271, 1984.

Preparation of 3',5'-O-(1,3-(1,1,3,3-tetraisopropyidisiloxanylidene))-5-(N-(4-methoxytriphenylmethyl)-5-amino-2(R,S)-phthalimido-oxypentyl)-2'-deoxyuridine (3.2)

This was prepared in an analogous manner to 3',5'-O-(1,3-(1,1,3,3-tetraisopropydisiloxanylidene))-5-(2-(R,S)-phthalimido-oxypropyl)-2'-deoxyuridine (2.2) starting with the alcohol (3.1) (2.35 g). Purification of the crude product by trituration in light petroleum/dichloromethane and repetitive flash column chromatography (ethyl acetate-chloroform-triethylamine 10:89:1–20:79:1 gradient) afforded the title compounds (3.2) (ca. 2.0 g) contaminated with triphenylphosphine oxide.

$\delta_H$(300 MHz; $CDCl_3$) 0.81–1.13 (28H, m, 4×$Me_2$CH), 1.61–1.87 (4H, m, 3"-$CH_2$ and 4"-$CH_2$), 2.06–2.19 (2H, m, 5"-$CH_2$), 2.35–2.50 (2H, m. 2'-$CH_2$), 2.50–2.81 (2H, m, 1"-$CH_2$), 3.68–3.83 (1H, m, 4'-CH), 3.76 (3H, s, Ar—OMe), 3.94–4.08 (2H, m, 5'-$CH_2$), 4.26–4.37 (0.5H, m, 2"-CH), 4.37–4.50 (0.5H, m, 2"-CH), 4.50–4.65 (1H, m, 3'-CH), 6.15 and 6.23 (each 0.5H, app. t, 1'-CH), 6.71–6.82 (2H, m, ArH), 7.08–7.84 (16.5H, m, 16 ArH+0.5 6-CH), 7.92 (0.5H, s, 6-CH) and 8.29 (1H, broad, NH) ppm.

Preparation of 1-(3,5-O-(1,3-(1,1,3,3-tetraisopropyldisiloxanylidene))-2-deoxy-β-D-ribofuranosyl)4-triazolo-5-(N-(4-methoxytriphenylmethyl)-5-amino-2(R,S)-phthalimido-oxypentyl)-1H-pyrimidin-2-one (3.3)

This was prepared in an analogous manner to 1-(3,5-O-(1,3-(1,1,3,3-tetraisopropyldisiloxanylidene))-2-deoxy-β-D-ribofuranosyl)4-triazolo-5-(2(R,S)-phthalimido-oxyhex-5-enyl)-1H-pyrimidin-2-one (2.3). Impure (3.2) (2.0 g) afforded the title compounds (3.3) (1.29 g) after flash column chromatography (ethyl acetate-light petroleum 80:20) as a sticky gum.

$\delta_H$(300 MHz; $CDCl_3$) 0.77–1.13 (28H, m, 4×$Me_2$CH), 1.42–1.98 (4H, m, 3"$CH_2$ and 4"$CH_2$), 2.03–2.19 (2H, m, 5"-$CH_2$), 2.35–2.50 (1H, m, 2'-CHH), 2.50–2.68 (1H, m, 2'-CHH), 2.76 (0.5H, dd, J 15.0 and 10.3 Hz, 1"-CHH), 2.98 (0.5H, dd, J 14.7 and 8.4 Hz, 1"-CHH), 3.41 (0.5H, dd, J 15.0 and 3.8 Hz, 1"-CHH), 3.63–3.77 (0.5H, m, 1 "-CHH), 3.70 (3H, s, ArOMe), 3.77–3.87 (1H, m, 4'-CH), 4.92–5.23 (3H, m, 5'-$CH_2$ and 2"-CH), 5.38 (1H, m, 3'-CH), 6.00 (0.5H, d, J 5.5 Hz, 1'-CH), 6.13 (0.5H, dd, J 7.3 and 1.8 Hz, 1'-CH), 6.73 (2H, m, ArH), 6.98–7.45 (12H, m, ArH), 7.58–7.74 (4.5H, m, 0.5×6-CH and 4×phthalimideH), 7.86 (0.5H, s, 6-H), 8.18, 8.31, 9.18 and 9.26 (each 0.5H, s, triazolideH) ppm.

Preparation of 6-(2-deoxy-β-D-ribofuranosyl)-3,4-dihydro-3(R,S)-(N-(4-methoxytriphenylmethyl)-3-aminopropyl)-8H-pyrimido[4,5-c][1,2] oxazin-7-one (3.4)

1-(3,5-O-(1,3-(1,1,3,3-Tetraisopropyldisiloxanylidene)))-2-deoxy-β-D-ribofuranosyl)4-triazole-5-(N-(4-methoxytriphenylmethyl)-5-amino-2(R,S)-phthalimido-oxypentyl)-1H-pyrimidin-2-one, (3.3) (1.29 g, 1.24 mmol) was reacted in an analogous way to example (2.4) to provide the title compounds (3.4) as a clear foam after silica gel flash chromatography using methanol dichloromethane, 5:95 as eluant. Yield 050 g. 68% Rf 0.31 in methanol:dichloromethane. 5:95 on silica t.l.c.

$\delta_H$(300 MHz; $CDCl_3$) 1.4–1.6(4H, m, $CH_2$-$CH_2$), 2.0–2.35(6H, sugar H2,H2', $CH_2$, $CH_2$N), 3.4(1H, m, NO—CH), 3.6–3.7(5H, m, $OCH_3$, sugar 2×H5), 3.8(1H, m, sugar H4), 4.37(1H, m, sugar H3), 6.05(1H, m, sugar H1), 6.6–6.7(3H, m, =CH, Ar 2×H), 7.0–7.3(12H, m, ArH) ppm.

Preparation of 6-(2-deoxy-β-D-ribofuranosyl)-3,4-dihydro-3(R,S)-(N(2,4-dinitrophenylacyl)-3-aminopropyl)-8H-pyrimido[4,5c][1,2]oxazin-7-one (3.6).

6-(2-Deoxy-β-D-ribofuranosyl)-3,4-dihydro-3(R,S)-(N-(4-methoxytriphenylmethyl)-3-aminopropyl)-8H-pyrimido[4,5-c][1,2]oxazin-7-one (3.4) (0.26 g, 4.35 mmol) was dissolved in acetonitrile (5 ml), acetic acid (8 ml) and water (2 ml) and left to stir at room temperature for 18 hours. T.l.c. (methanol: $CHCl_3$ 1:9) indicated that amine deprotection had gone to completion and that the free amino compound (3.5) remained on the baseline. The reaction solvent was then removed under reduced pressure and the last traces of acetic acid removed by co-evaporation with toluene (x3) followed by co-evaporation with toluene plus triethylamine (0.5 ml) (x3). The residual gum was redissolved in $CH_2Cl_2$ (10 ml) and DMF (10 ml) and the N-hydroxysuccinimidyl ester of 2,4-dinitrophenylacetic acid (300 mg, 0.93 mmol) was added and the reaction allowed to stir at room temperature for two hours. The reaction solvent was removed by exhaustive co-evaporation with toluene. The product was purified by an initial silica gel flash chromatography column using $CHCl_3$:methanol:water, 80:18:2 followed by a final hplc purification using a PRP-1 column and an acetonitrile::water gradient to give the title compounds (3.6) as a pale yellow gum. Yield 136 mg 59% Rf 0.2 in methanol:$CHCl_3$ 1:9 on silica t.l.c.

$\delta_H$(300 MHz;$CD_3OD$) 1.6–1.8(4H, m. $CH_2CH_2$), 2.15 (2H, m, =CH—C$\underline{H}_2$), 2.35(1H, m, sugar H2), 2.65(1H, m, sugar H2), 3.3(2H, m, $CH_2$NHC(O)), 3.6–3.8(3H, m, sugar 2×H5, =N—O—CH), 3.85(1H, m, sugar H4), 407(2H, s, C(O)—$CH_2$—Ar). 4.35(1H, m, sugar H3), 6.25(1H, m, sugar H1), 7.09(1H, s, =CH), 7.74(1H, d, ArH, J8.4 Hz), 8.46(1H, dd, ArH, J8.4, 2.2 Hz), 8.83(1H, d, ArH, J 2.2 Hz) ppm.

By standard methodology the above can be converted to a phosphoramidite as required see P. K. T. Lin and D. M. Brown, *Nucleic Acids Res.* 17, 10373 (1989).

Preparation of 6-(2-deoxy-β-D-ribofuranosyl)-3,4-dihydro-3(R,S)-(N-(6-(fluorescein-5-(and-6)-carboxamidohexanoyl))-3-aminopropyl)-8H-pyrimido[4,6-c][1,2]oxazin-7-one (3.7).

6-(2-deoxy-β-D-ribofuranosyl)-3,4-dihydro-3(R,S)-(N-(4-methoxytriphenylmethyl)-3-aminopropyl)-8H-pyrimido[4,5-c][1,2]oxazin-7-one (3.4) (44 mg, 0.082 mmol) was deprotected in an analogous manner as example (3.6), and the free amino group reacted with fluorescein-5(6)-carboxamidocaproic acid N-hydroxsuccinimide ester (65 mg, 0.11 mmol). Product purification was achieved by silica gel flash chromatography using $CHCl_3$:methanol:water, 10:5:1 as eluant to yield the title compound as an orange gum. Yield 39 mg, 49%, Rf 0.49 in $CHCl_3$:methanol:water, 10:5:1 on silica t.l.c.

$\delta_H$(300 MHz; $CDCl_3$) 1.3–1.7(1OH, m, —$CH_2$—), 2.1–2.35(5H, m, $CH_2$C(O), =CH—C$\underline{H}_2$, sugar H2), 2.55 (1H, m, sugar H2'), 3.1–3.2(2H, m, $CH_2$NHC(O)), 3.3–3.4 (2H, m, $CH_2$NH(O)Ar), 3.5–3.×(3H, m, sugar 2×H5, =N—O—CH), 3.8(1H, m, sugar H4), 4.35(1H, m, sugar H3), 6.25(1H, m, sugar H1), 6.5–8.4(10H, series of m, ArH, =CH) ppm.

EXAMPLE 4
Preparation of 6-(-2-deoxy-β-D-ribofuranosyl -3 4-dihydro-3(R,S)-but-5-enyl-8H5pyrimido[4,5c][1,2] oxazin-7-one (4.4)
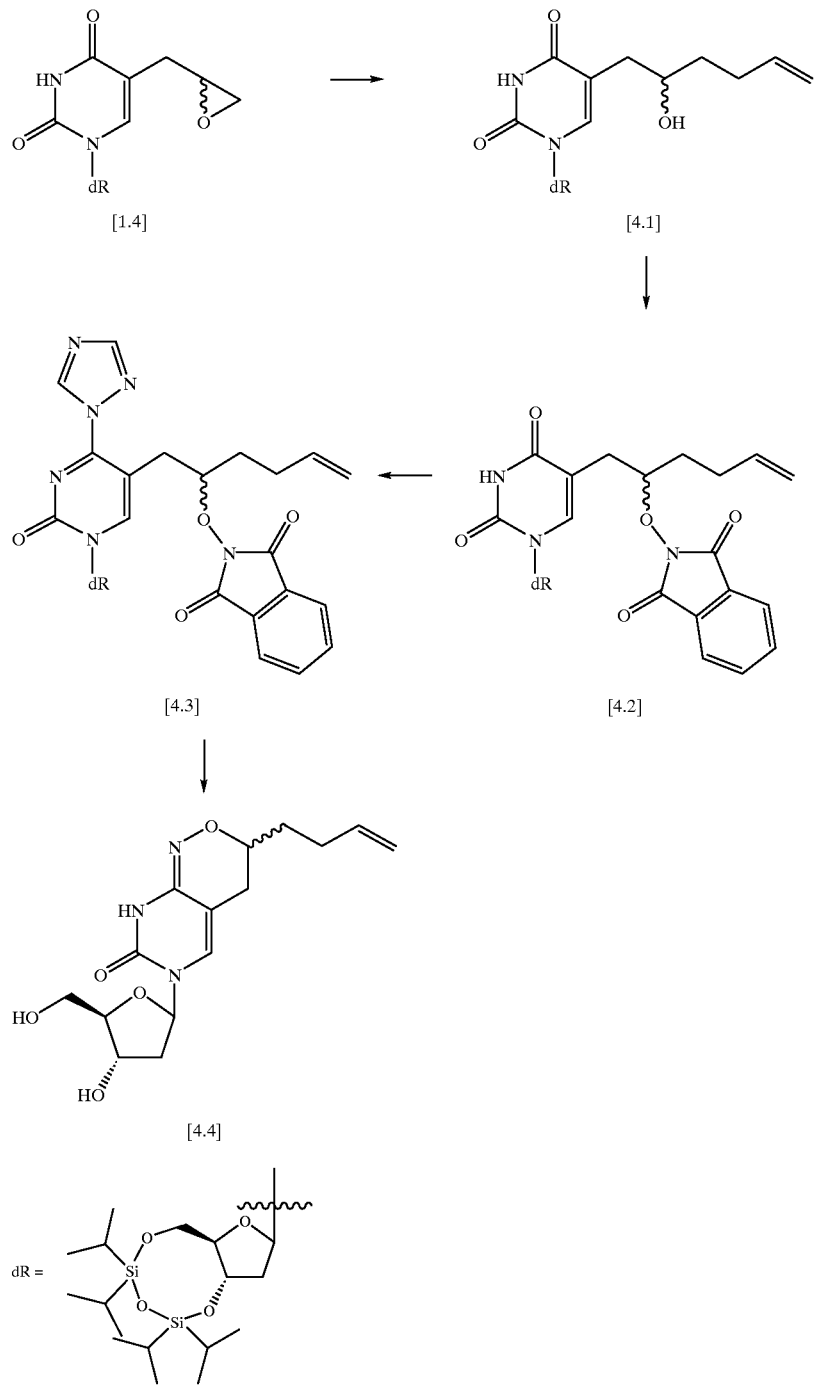

Preparation of 3',5'-O-(1,3-(1,1,3,3-tetraisopropyidisiloxanylidene))-5-(2-(R,S)-hydroxyhex-5-enyl)-2'-deoxyuridine (4.1)

Allylmagnesium chloride (25 ml of a 2.0 M solution in THF, 50 mmol) was added dropwise, over 15 min, to a stirred slurry of copper (I) bromide-dimethyl sulphide complex (10.3 g, 50.3 mmol) in THF (132 ml) at −78° C. After 40 min a cooled, −78° C., solution of the epoxide (1.4) (4.41 g, 8.38 mmol) in THF (80 ml) was added via a cannula over 15 min, followed by a THF wash (10 ml). The reaction mixture was allowed to stir at −78° C. for a further 70 min after which the cooling bath was removed and the reaction mixture was allowed to warm to ambient over a period of 60 min. The mixture was then added via a cannula to a vigorously stirred mixture of $Et_2O$ (250 ml), saturated $NH_4Cl$ (aq) (230 ml) and conc. $NH_4OH$ (20 ml). The reaction vessel was washed with a mixture of $Et_2O$ (20 ml), saturated $NH_4Cl$ (aq) (20 ml) and conc. $NH_4OH$ (20 ml) which was added to the rest of the material. The mixture was then stirred for a further 30 min and diluted with $Et_2O$. The aqueous phase was separated, exhaustively extracted with $Et_2O$ and the combined organic phase was washed with brine, dried ($MgSO_4$) and concentrated in vacuo. Both TLC and $^1H$ nmr evidence suggested that the required product was contaminated with a substantial amount of the bromohydrin. Brief treatment of the crude material with methanolic $K_2CO_3$, followed by a standard extractive work up, afforded a crude mixture containing the starting epoxide (1.4), the required title compounds (4.1) and other material thought to be due to partial cleavage of the siloxy moiety. Flash column chromatography of the crude product (dichloromethane-methanol 100:0–95:5 gradient) afforded the title compound contaminated with the starting epoxide (2.72 g total).

$δ_H$(300 MHz; $CDCl_3$) 0.82–1.16 (28H,m,4×$Me_2CH$), 2.00–2.58 (8H, m ,2'-$CH_2$, 1"+3"+4"-$CH_2$), 3.68–3.82 (1H, m, 4'-CH), 3.93–4.13 (2H, m, 5'-$CH_2$), 4.42–4.58 (1H, m, 3'-$CH_2$), 4.90–5.10 (2H, m, 6"-$CH_2$), 5.73–5.90 (1H, m, 5"-CH), 7.39 and 7.44 (each 0.5H, s, 6-CH) and 8.18 (1H, br s, NH) ppm.

Preparation of 3',5'-O-(1,3-(1,1,3,3-tetraisopropyidisiloxanylidene))-5-(2-(R,S)-phthalimido-oxyhex-5-enyl)-2'-deoxyuridine (4.2)

This compound was prepared in an analogous manner to 3',5'-O-( 1,3-(1,1,3,3-tetraisopropyidisiloxanylidene))-5-(2-(R,S)-phthalimido-oxypropyl)-2'-deoxyuridine (2.2) using 3',5'-O-(1,1,3,3,-tetraisopropyidisiloxanylidene))-5-(2-(R,S)-hydroxyhex-5-enyl)-2'-deoxyuridine (4.1) contaminated with the epoxide (1.4) (2.70 g total). Repetitive flash column chromatography (ethyl acetate-light petroleum 1:5–7:3 gradient and dichloromethane-methanol 100:0–98.5:1.5 gradient) followed by trituration in hexane/dichloromethane, filtration and concentration of the filtrate afforded the title compounds (4.2) (3.32 g) as a white solid, which was still contaminated with the epoxide (1.4).

$δ_H$(300 MHz; $CDCl_3$) 0.77–1.16 (28H, m, 4×$Me_2CH$), 2.18–2.68 (8H, m, 2'-$CH_2$, 1"+3"+4"-$CH_2$), 3.68–3.85 (1H, m, 4'-CH), 3.95–4.11 (2H, m, 5'-$CH_2$), 4.35–4.63 (1H, m, 3'-CH), 4.90–5.13 (2H, m, 6"-$CH_2$), 5.81 (1H, m, 5"-CH), 6.13 and 6.23 (each 0.5H, m, 1'-CH), 7.39 and 7.44 (each 0.5H, s, 6-CH), 7.71–7.84 (4H, m, ArH) and 8.16–8.27 (1H, broad, NH) ppm.

Preparation of 1-(3,5-O-(1,3-(1,1,3,3-tetraisopropyidisiloxanylidene))-2-deoxy-β-D-ribofuranosyl)-4-triazolo-5-(2(R,S)-phthalimido-oxyhex-5-enyl)-1H-pyrimidin-2-one (4.3)

This was prepared in an analogous manner to 1-(3,5-O-(1,3-(1,1,3,3-tetraisopropyidisiloxanylidene))-2-deoxy-β-D-nbofuranosyl)4-triazolo-5-(2(R,S)-phthalimido-oxyhex-5-enyl)-H-pyrimidin-2-one (2.3) using the impure 2'-deoxyuridine (4.2) (3.3 g). Reaction progress was monitored by TLC ( ethyl acetate) and upon completion the mixture was filtered and the solids washed with $Et_2O$ The filtrate was concentrated in vacuo and the residue was subjected to a standard extractive work up ($Et_2O/H_2O$). Flash chromatography (ethyl acetate-light petroleum 1:1–7:3 gradient) of the crude product afforded the title compounds (4.3) (1.33 g pure and 1.1 g of impure material) as sticky solids.

$δ_H$(300 MHz; $CDCl_3$) 0.81–2.16 (28H, m, 4×$Me_2CH$), 1.69–2.05 (2H, m, 3"-$CH_2$), 2.05–2.55 (3H, m, 4"-$CH_2$+ 2'CHH), 2.55–2.71 (1H, m, 2'-CHH), 2.85 (0.5H, dd, J 15.0 and 9.9 Hz, 1"-CHH), 3.05 (0.5H, dd, J 14.7 and 8.4 Hz, 1"-CHH), 3.47(0.5H, dd, J 14.8 and 4.1 Hz, 1"-CHH, 3.71 (0.5H, dd, J 14.9 and 2.6 Hz, 1"-CHH), 3.79–3.90 (1H, m, 4'-CH), 3.94–4.24 (3H, m, 5'-$CH_{2+2}$'-CH), 4.39 (1H, m, 3'-CH), 4.90–5.10 (2H, m, 6"-$CH_2$), 5.79 (1H, m, 5"-CH), 6.04 (0.5H, dd, J6.7 and 1.5 Hz, 1'-CH), 6.17 (0.5H, dd, J 7.4 and 2.10 Hz, 1'-CH), 7.65–7.81 (4.5H, m, 4×ArH+0.5 6-CH), 7.95 (0.5H, s, 6-CH), 8.21, 8.33, 9.23 and 9.30 (each 0.5H, s, triazolide H) ppm.

Preparation of 6-(2-deoxy-β-D-ribofuranosyl)-3,4-dihydro-3(R,S)-but-5-enyl-8H-pyrimido[4,5c][1,2]oxazin-7-one (4.4)

This was prepared in an analgous manner to 6-(2-deoxy-β-β-ribofuranosyl)-3,4-dihydro-3(R,S)-methyl-8H-pyrimido[4,5c][1,2]oxazin-7-one (2.4). Triazolide (4.3) (1.30 g) afforded, after flash column chromatography (dichloromethane-methanol 99:1–95:5 gradient) the protected cyclised material as a sticky foam (930 mg).

Partial proton NMR data: $δ_H$(300 MHz; $CDCl_3$) 0.85–1.20 (28H, m, 4×$Me_2CH$), 1.53–1.69 (1H,m, 1"-CHH), 1.75–1.90 (1H, m, 1"-CHH), 2.12–2.61 (6H, m, 3'-$CH_2$+4-$CH_2$+2"-$CH_2$), 4.03 (2H, m, 5'-$CH_2$), 4.46 (1H, m, 3'CH), 4.95–5.14 (2H, m, 6"-$CH_2$), 5.83 (1H, m, 5"-CH), 6.08 (1H, m, 1'-CH), 6.73 and 6.76 (each 0.5H, s, 6-CH) and 8.53 (1H, br s, NH)

Treatment of a portion of this material (ca. 450 mg) with tetra-n-butylammonium fluoride furnished the title compounds (4.4) (200 mg), as a sticky gum, after flash column chromatography (dichloromethane-methanol 95:5–90:10 gradient).

UV $λ_{max}$ (MeOH) 204, 232 and 298 nm $δ_H$(300 MHz;$CD_3OD$) 1.53–1.79 (2H, m, 1"-$CH_2$), 2.10–2.45 (5H, m, 4-CHH+2'-$CH_2$+2"-$CH_2$), 2.65 (1H, br d, J 14.4 Hz, 4-CHH), 3.5–3.82 (3H, m, 3-CH+5'-CH2) 3.87 (1H, m, 4'-CH), 4.35 (1H, m, 3'-CH), 4.96 (1H, br d, J 10.3 Hz, 4"-CHH), 5.04 (1H, dd, J 16.9 and 1.7 Hz, 4"-CHH), 5.74 (1H, ddt, J 16.9,10.3 and 6.6 Hz, 3"-CH), 6.26 (1H, m, 3'-CH), 7.1 (1H, s, 4-H) ppm.

$δ_c$(75 MHz; $CD_3OD$) 30.24, 30.38, 30.50, 33.96, 34.01, 40.53, 62.99, 72.32, 72.34, 75.95, 85.53, 88.36,101.70, 101.76, 115.52, 130.46, 139.07, 151.44, 151.51, 152.63 and 152.65 ppm.

EXAMPLE 5

Synthesis of 6-(2-deoxy-β-D-ribofuranosyl)-3,4-dihydro-3(R,S)-(3,3-diO-(1,3-propylidene)-propyl)-8H-pyrimido[4,5c][1,2]oxazin-7-one

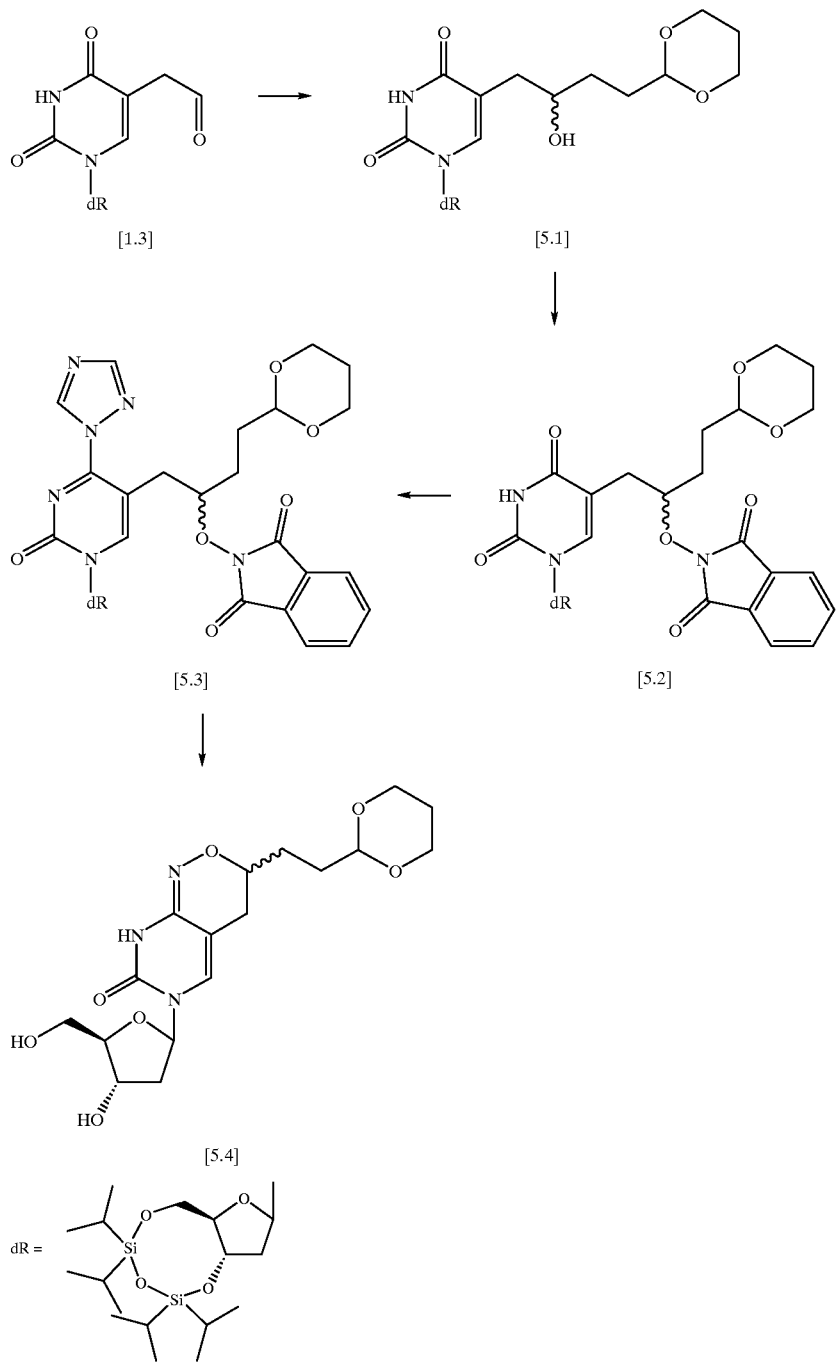

Preparation of 3',5'-O-(1,3-(1,1,3,3-tetraisopropyidisiloxanylidene))-5-(5,5-diO-(1,3-propylidene)-2(R,S)-hydroxypentyl)-2'-deoxyuridine (5.1)

Into an oven-dried 3-neck 50 ml flask were added magnesium turnings (0.60 g, 25 mgram atom) and dry diethyl ether (5 ml), and the mixture set stirring under an argon atmosphere. To this was added a solution of freshly distilled 2-(2-bromoethyl)-1,3-dioxane (4.88 g, 25 mmol) in dry tetrahydrofuran (15 ml), in portions so as to control the exothermic reaction that ensued. Once all the bromide had been added the reaction was allowed to subside before being heated at reflux for 30 minutes (hot water bath). By the end of this time almost all of the magnesium had been consumed to give a pale yellow solution.

About half of this solution (12 mmol Grignard reagent) was transferred to a second dry, argon-filled flask. To this was added a solution of 3',5'-O-(1,3-(1,1,3,3-tetraisopropyldisiloxanylidene))-5-(carbonylmethyl)-2'-deoxyuridine (1.3) (1.64 g, 3.2 mmol) in dry tetrahydrofuran (5 ml) and acetic acid (40 µl). The resulting mixture was stirred for 30 minutes, then quenched with saturated aqueous ammonium chloride solution and extracted with diethyl ether. The combined ether extracts were dried (Na$_2$SO$_4$), filtered and evaporated under reduced pressure to a yellow oil. Purification by flash column chromatography (silica; 25% light petroleum/ethyl acetate) gave the title compound (5.1) as an off-white foam, 1.37 g (68%). UV (CHCl$_3$) 270 nm.

$\delta_H$(300 MHz; CDCl$_3$) 0.8–1.1 (28H, m, Si—iPr×4), 1.31 (1H, m, propylidene O-CH$_2$-CHH-CH$_2$-O), 1.40–1.75 (5H, m), 2.06 (1H, m, propylidene O-CH$_2$-CHH-CH$_2$-O), 2.23–2.58 (4H, m), 3.28 (1H, broad t, OH), 3.70–3.78 (4H, m, sugar 4'+-CHOH +propylidene O-CH$_2$-CHH-CH$_2$-O), 4.00–4.10 (4H, m, sugar 5'+propylidene O-CH$_2$-CHH-CH$_2$-O), 4.48 (1H, m, sugar 3'), 4.56 (1H, t, J4.5 Hz, acetal O-CH-O), 6.05 (1H, m, sugar 1'), 7.36+7.42 (1H, 2s, C6 diastereomers), 8.60+8.62 (1H, 2s, N3 diastereomers) ppm.

Preparation of 3',5'-O-(1,3-(1,1,3,3-tetraisopropyldisiloxanylidene))-5-(5,5-diO-(1,3-propylidene)-2(R,S)-phthalimido-oxypentyl)-2'-deoxyuridine (5.2)

Prepared as for 3',5'-O-(1,3-(1,1,3,3-tetraisopropyldisiloxanylidene))-5-(2-(R,S)-phthalimido-oxypropyl)-2'-deoxyuridine (2.2). UV (CHCl$_3$) 242, 268 nm.

$\delta_H$(300 MHz; CDCl$_3$) 0.86–1.11 (28H, m, Si—iPr×4), 1.23–1.30 (1H, m, propylidene O-CH$_2$-CHH-CH$_2$-O), 1.70–2.10 (5H, m), 2.37–2.71 (4H, m), 3.66–3.81 (3H, m, sugar 4'+propylidene O-CH$_2$-CHH—CH$_2$O), 3.96–4.08 (4H, m, sugar 5'+propylidene O—CH$_2$-CHH-CH$_2$-O), 4.33–4.50 (1H, 2m, -CH(O-phthalimide) diastereomers), 4.50–4.60 (2H, m, sugar 3'+acetal O—CH-O), 6.13+6.22 (1H, 2 apparent t, sugar 1' diastereomers), 7.70–7.86 (5H, m, C6+phthalimide 4H), 8.44+8.46 (1H, 2s, N3 diastereomers).

Preparation of 1-(3',5'-O-(1,3-(1,1,3,3-tetraisopropyidisiloxanylidene))-2-deoxy-β-D-ribofuranosyl)4-triazolo-5-(5,5-diO-(1,3-propylidene)-2(R,S)-phthalimido-oxypentyl)-1H-pyrimidin-2-one (5.3)

Prepared as for 1-(3',5'-O-(1,3-(1,1,3,3-tetraisopropyldisiloxanylidene))-2-deoxy-β-D-ribofuranosyl)-4-triazolo-5-(2-(R,S)-phthalimido-oxypropyl)-1H-pyrimidin-2-one (2.3). Used directly in the next step.

Preparation of 6-(2-deoxy-β-D-ribofuranosyl)-3,4-dihydro-3(R,S)-(3,3-diO-(1,3-propylidene)-propyl)-8H-pyrimido[4,5c][1,2]oxazin-7-one (5.4)

Prepared as for 6-(2-deoxy-β-D-ribofuranosyl)-3,4-dihydro-3(R,S)-methyl-8H-pyrimido[4,5c][1,2]oxazin-7-one (2.4). Triazolide (5.3) (0.50 g) afforded, after treatment with 1,4-dioxan saturated with ammonia, and purification by flash column chromatography (silica; 40% ethyl acetate/dichloromethane), the protected cyclised product (0.28 g). UV (CHCl$_3$) 302 nm. $\delta_H$(300 MHz; CDCl$_3$) 0.89–1.07 (28H, m, Si—iPr×4), 1.31 (1H, m), 1.50–2.53 (9H, m), 3.65–3.78 (4H, m, sugar 4'+ring 3-H+propylidene O-CH$_2$-CHH—CH$_2$-O), 3.94–4.10 (4H, m, sugar 5'+propylidene O—CH$_2$-CHH-CH$_2$-O), 4.43 (1H, m, sugar 3'), 4.55 (1H, broad t, acetal O—CH-O), 6.03 (1H, m, sugar 1'), 6.66+6.69 (1H, 2s, C5 diastereomers), 7.5–8.0 (1H, broad s) ppm.

Treatment of this material with tetra-n-butylammonium fluoride gave the title compounds (100 mg). Complete removal of the tetra-n-butylammonium ions was not possible.

EXAMPLE 6

Synthesis of 6-(2-deoxy-β-D-ribofuranosyl)-3,4-dihydro-8H-pyrimido[4.5-c][1,2]pyridazin-7-one (6.4) and 5-(2-chloroethyl)-1-(2',3'-isopropylidine-β-D-ribofuranosyl)uridine (6.8)

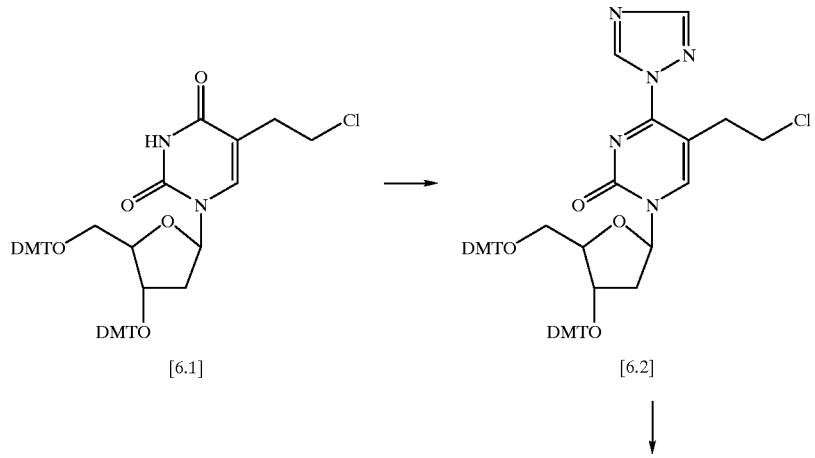

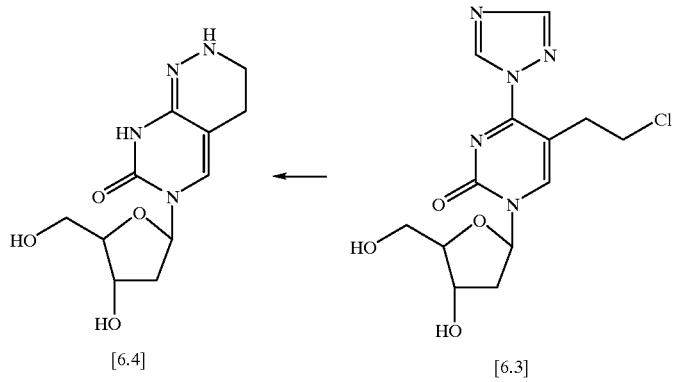

[6.4]   [6.3]

Preparation of 5-(2-chloroethyl)-1-(3',5'-diO-dimethoxytrityl-2'-deoxy-β-D-ribofuranosyl)uridine (6.1)

5-(2-Chloroethyl)-2'deoxyuridine (2 g, 6.9 mmol) was dissolved in pyridine (40 ml) and dimethoxytrityl chloride (79, 21 mmol) added and the solution heated at 50° C. overnight. The solvent was evaporated and the product dissolved in chloroform and washed with sodium bicarbonate solution, dried and evaporated under reduced pressure to a yellow gum which was chromatographed (CHCl3) to give a yellow foam. Yield 5.8 g, 94%.

Preparation of 1-(3',5'-diO-dimethoxytrityl-2'-deoxy-β-D-ribofuranosyl)-4-(1,2,4-triazolo)-5-(2-chloroethyl)-pyramid-2-one (6.2).

To an ice-cold suspension of 1,2,4-triazole (6.4 g, 9.3 mmol) in acetonitrile (100 ml) was added phosphorous oxychloride (1.7 ml, 2.8 mmol) and the solution stirred at 0° C. for 15 minutes. To this was then added triethylamine (1 5.5 ml, 11.2 mmol) and the solution stirred for a further 15 minutes. The tritylated nucleoside (6.1) (5.5 g, 6.1 mmol) in acetonitrile (25 ml) was added and the solution stirred at room temperature overnight. The solvent was removed and the product dissolved in chloroform and washed (sodium bicarbonate), dried (sodium sulphate) and evaporated to a brown gum which was chromatographed (CHCl3) to give a yellow foam. Yield 6.1 g, 105%.

Preparation of 1-(2-deoxy-β-D-ribofuranosyl)4-(1,2,4-triazolo)-5-(2-chloroethyl)-pyramid-2-one (6.3).

To a solution of the above nucleoside (6.2) (6 g, 6.3 mmol) in dichloromethane (100 ml) was added trichloroacetic acid (5.2 g, 32 mmol) and the solution stirred at room temperature overnight. The solution was concentrated and chromatographed (CHCl3 then CHCl3/5% MeOH) to give a white solid. Yield 1.73 g, 80%.

$\delta_H$(DMSO-d6) 2.09–2.17, 2.35–2.41 (2H, m, H2', H2"), 3.20–3.30 (2H, m, C5-CH2), 3.58–3.77 (4H, m, H5', H5", CH2Cl), 3.89–3.93 (1H, m, H3'), 4.23–4.28 (1H, m, H4'), 5.23 (1H, br. s, OH), 5.32 (1H, br. s, OH), 6.11 (1H, t, J 5.9 Hz, H1'), 8.40 (1H, s, triazolo CH), 8.69 (1H, s, H6), 9.33 (1H, s, triazolo CH) ppm. UV $\lambda_{max}$ 321 ($\epsilon$=5600), 249 ($\epsilon$=6500), $\epsilon$260 ($\mu$M)=4.9. pH 12 (irreversible) $\lambda_{max}$ 267.

A small amount of the triazolo nucleoside (6.3) was dissolved in acetonitrile and treated with anhydrous hydrazine to give the bicyclic product (6.4). UV $\lambda_{max}$ 280 ($\epsilon$=14800).

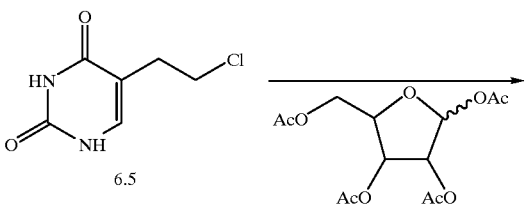

6.5

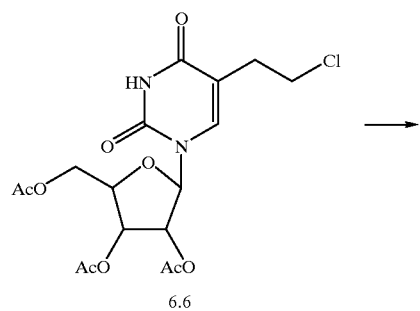

6.6

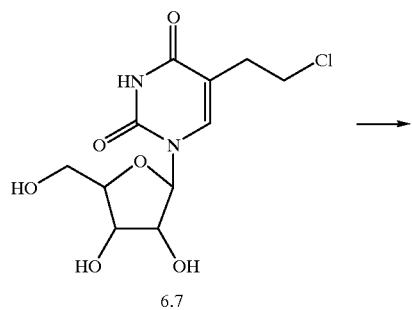

6.7

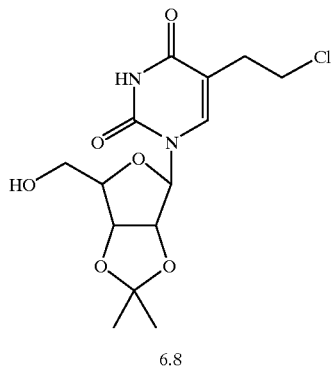

6.8

Preparation of 5-(2-chloroethyl)-1-(2',3',5'-tri-O-acetyl-β-D-ribofuranosyl)uridine (6.6)

5-(2-Chloroethyl)uracil (6.5) (0.5 g, 2.9 mmol), formed by the method of Griengl (J Med Chem vol 28, pp1679–1684, 1985), was heated at 120° C. overnight with hexamethyldisilazane (20 ml) and chlorotrimethisilane (1.5 ml). This was cooled to room temperature and evaporated, then coevaporated with dry xylene( 3×25 ml) and then dissolved in dry acetonitrile (25 ml). 1,2,3,5-tetra-O-acetyl ribose (1.0 g, 3.1 mmol) was dissolved in dry acetonitrile (25 ml) and then sodium iodide (1.29 g, 8.6 mmol) added and allowed to dissolve. To this was then added chlorotrimethylsilane (0.55 ml, 4.3 mmol) and the solution stirred at room temperature for 20 minutes. This was then added to the silylated base and the whole stirred at room temperature for 2 hours. TLC shows one major spot. The solution was then evaporated redissolved in chloroform and extracted firstly with sodium bicarbonate solution and then with sodium thiosulphate solution, dried and evaporated to dryness. The residue was lo then purified by column chromatography (silica, chloroform to chloroform/2% methanol gradient) to isolate the product as a white foam. Products were observed on t.l.c. by staining with p-anisaldehyde solution (anisaldehyde, sulphuric acid, ethanol;1:1:10) and heating the plate. Yield 0.88 g, 71%.

$\delta_H$(DMSO-d6) 2.00, 2.04, 2.07(9H, 3×s, 3×COCH$_3$), 2.66 (2H, t, J6.9 Hz, 5-CH$_2$), 3.70(2H,t, J6.9Hz, CH$_2$Cl), 4.18–4.33(3H, m), 5.31–5.36(1H, m), 5.41–5.45(1H,m), 5.89(1H, d, J 5.2 Hz, 1'-CH), 7.66(1H, s, 6-CH), 11.56(1H, s, NH) ppm.

Preparation of 5-(2-chloroethyl)-1-(β-D-ribofuranosyl)uridine (6.7) 5-(2-chloroethyl)-1-(2',3',5'-tri-O-acetyl-β-D-ribofuranosyl)uridine (15 g, 34.76 mmol) was dissolved in a solution of potassium carbonate (0.5M in methanol/water, 3:1) (350 ml). After 2 hours, t.l.c. (dichloromethane/methanol, 9:1) showed that all starting material had been converted to a product near the baseline. Prewashed Dowex 50 W X8 ion exchange resin (H+ form) was added to neutralise the base as verified by the pH of the solution. The solid resin was filtered off and washed with a portion of methanol/water. 3:1. Methanol was evaporated off in vacuo and the solution diluted with water (300 ml). The aqueous solution was than extracted with dichloromethane (2×100 ml) and the aqueous layer evaporated to dryness. The solid residue was then recrystallized from ethanol, yielding colourless title compound (6.7) which was homogeneous by hplc (mp158–160° C.). Yield 7.7 g, 76%.

Preparation of 5-(2-chloroethyl)-1-(2',3'-isopropylidine-β-D-ribofuranosyl)uridine (6.8) 5-(2-chloroethyl)-1-(β-D-ribofuranosyl)uridine (6.7) (0.85 g, 2.8 mmol) was dissolved in acetone (30 ml) and p-toluene sulphonic acid hydrate (0.506 g, 2.66 mmol) was added, followed by triethyl orthoformate (1.66 g, 11.2 mmol). The initially insoluble nucleoside dissolved within 15 minutes to give a slightly yellow solution. After stirring for 2.5 hours t.l.c. (dichloromethane/methanol; 9:1) showed that all starting material had been converted to a new spot Rf 0.52 The volatile material was evaporated off in vacuo and the residue treated with dipotassium hydrogen phosphate solution (25 ml of aqueous solution containing 0.815 g phosphate) and extracted with ethyl acetate (2×30 ml). The organic extract was washed with water (2×40 ml) followed by brine (40 ml) and the organic layer dried over sodium sulphate. After filtering and evaporation of the extract to dryness, the product was purified by chromatography over silica gel eluting with dichloromethane/acetonitrile 7:3 to yield title compound as a colourless solid (0.8 g, 86%). T.l.c. (dichloromethanel acetonitrile; 7:3, Rf 0.21); purity by h.p.l.c. (C-18 column, 40% acetonitrile, 60% 0.1M triethylammonium acetate)>98%.

$\delta_H$(CDCl$_3$) 7.54(1H, s), 5.75(1H, d), 4.81(2H, m), 4.18 (1H, m), 3.80–3.55(4H, m), 2.66(2H, m), 1.49(3H, s), 1.26 (3H, s) ppm. $\delta_{13C}$ (CDCl$_3$) 163.488 (C), 150.367(C), 139.650(CH), 113.759(C), 110.271(C), 92.957(CH), 86.480 (CH), 84.108(CH), 80.352(CH), 61.952(CH$_2$), 42.683 (CH$_2$), 30.352(CH$_2$), 27.069(CH$_3$) 25.139(CH$_3$).

EXAMPLE 7

Synthesis of 2-benzyl-6-(2-deoxy-β-D-ribofuranosyl)-3,4-dihydro-8H-pyrimido[4,5-c][1,2] 1pyridazin-7-one and 2-(3-hydroxybenzyl)-6-(3.5-di-O-p-toluoyl-2-deoxy-β-D-ribofuranosyl)-3,4-dihydro-8H-pyrimido[4,5-c][1,2pyridazin-7-one

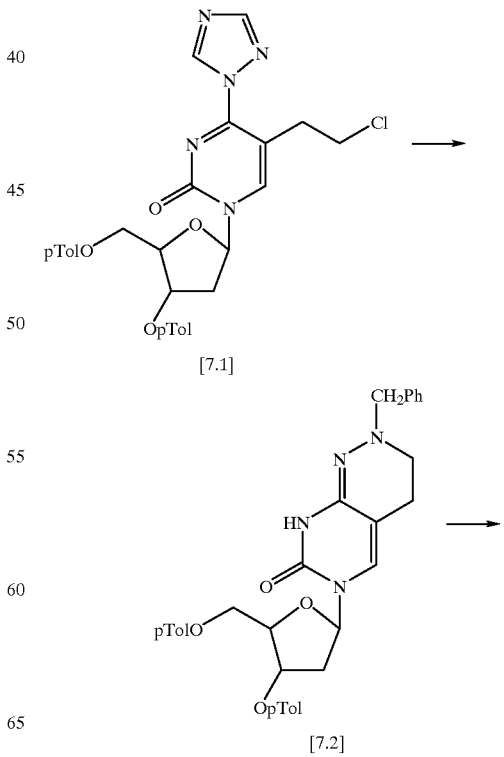

-continued

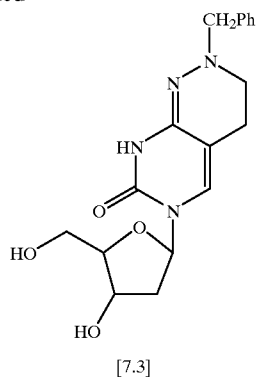

[7.3]

Preparation of 1-(3,5-di-O-p-toluoyl-2-deoxy-β-D-ribofuranosyl)4-(1,2,4-triazolo)-5-(2-chloroethyl)-pyrimid-2-one (7.1).

1,2,4-Triazole (12.1 g, 176 mmol) was suspended in acetonitrile (250 ml) at 0° C. and to this was added phosphorous oxychloride (3.8 ml, 40 mmol) and the solution stirred at 0° C. for 15 minutes. To this was then added triethylamine (30 ml, 214 mmol) and the solution stirred at 0° C. for a further 30 minutes. To this was then added a solution of 3',5'-di-O-p-toluoyl-2'-deoxyribofuranosyl-5-(2-chloroethyl)-uracil (5.3 g, 10.5 mmol) in acetonitrile (50 ml) and the solution stirred at room temperature overnight. The solution was evaporated, dissolved in chloroform and washed with aqueous sodium bicarbonate, dried and evaporated to a gum, which was purified by chromatography (CHCl$_3$/2% MeOH) to give a white foam. Yield 5.82 g, 96%.

$δ_H$ 1.7 (1H, s, ), 2.35 (3H, s, ), 2.42 (3H, s, ), 3.16 (1H, s,), 3.20 (2H, ), 3.65 (2H, ), 4.68 (1H, d, ), 4.70 (1H, ), 4.88 (1H, ), 5.60 (1H,), 6.35 (1H, ), 7.18 (2H, ), 7.25 (2H), 7.82 (2H, ), 7.95 (2H, ), 8.15 (1H,), 8.20 (1H, ), 9.3 (1H, ) ppm. FAB mass 578.4, C$_{29}$H$_{28}$ClN$_5$O$_6$ requires 577.5, Accurate mass measurement 577.17279.

Preparation of 2-benzyl-6-(3,5-di-O-p-toluoyl-2-deoxy-β-D-ribofuranosyl)-3,4-dihydro-8H-pyrimido[4,5-c][1,2]pyridazin-7-one (7.2).

To a solution of the above triazole (7.1) (6.35 g, 11 mmol) and benzylhydrazine dihydrochloride (2.35 g, 12.1 mmol) in ethanol (200 ml) was added triethylamine (6 ml) and the solution heated at reflux overnight. The solution was evaporated and chromatographed (EtOAc:hexane 1:1 then CHCl$_3$/MeOH 2–5%) to give 4 products. Product 1 was identified as the C$^4$-O-ethyl derivative (0.76 g), compound 3 as the 5-membered cyclised product (2.9 g), compound 4 is un-identified (3.1 g). Compound 2 was identified as the desired product (1.29 g. 20%); $δ_H$ (DMSO-d6) 2.23–2.56 (6H, m, CH$_2$N, C5-CH$_2$, H2', H2"), 2.35 (3H, s, CH$_3$), 2.37 (3H, S, CH$_3$), 3.92 (2H, s, CH$_2$Ph), 4.36–4.38 (1H, m, H4'), 4.46–4.61 (2H, m, H5', H5"), 5.52–5.54 (1H, m, H3'), 6.26 (1H, t, J6.5 Hz, H1'), 6.58 (1H, s, H6), 7.21–7.35 (9H, m, PhthCH, ArCH), 7.86–7.91 (4H, m, ArCH), 10.13 (1H, s, NH) ppm. FAB mass 595.2 (M+H).

Preparation of 2-benzyl-6-(2-deoxy-β-D-ribofuranosyl)-3,4-dihydro-8H-pyrimido[4,5-c][1,2]pyridazin-7-one (7.3).

The above compound (7.2) (1.4 g, 2.35 mmol) was suspended in methanol (50 ml) and to this was added sodium methoxide (140 mg, 2.6 mmol) and the solution stirred at room temperature for 1 hour. The solvent was removed and the product chromatographed (CHCl$_3$/10% MeOH) to give a pale yellow powder. Yield 0.61 g, 72%. $δ_H$ 1.88–2.03 (2H, m, H2', H2"), 2.45–2.50 (2H, m, CH$_2$N), 2.59–2.63 (2H, m, CH$_2$C(5)), 3.41–3.54 (2H, m, H5', H5"), 3.65–3.66 (1H, m, H4'), 3.92 (2H, s, CH$_2$Ph), 4.16 (1H, m, H3'), 4.89 (1H, t, 5'-OH), 5.15 (1H, d, 3'-OH), 6.13 (1H, t, J6.1 Hz, H1'), 6.74 (1H, s, H6), 7.21–7.34 (5H, m, Ph), 9.98 (1H, s, NH) ppm. UV λ$_{max}$ 295 (ε=7800). ε260 (μM)=5.7

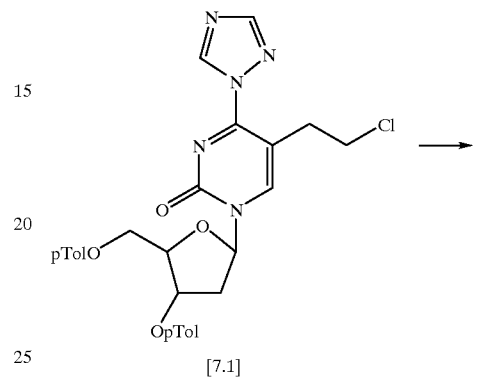

[7.1]

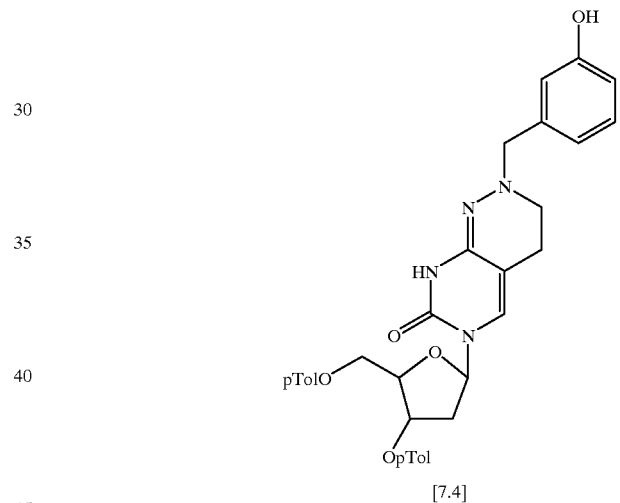

[7.4]

Preparation of 2-(3-hydroxybenzyl)-6-(3,5-di-O-p-toluoyl-2-deoxy-β-D-ribofuranosyl)-3,4-dihydro-8H-pyrimido[4,5-c][1,2]pyridazin-7-one (7.4).

To a solution of the triazole (7.1) (1 g, 1.7 mmol) and 3-hydroxybenzylhydrazine dihydrochloride (0.73 g, 3.5 mmol) in ethanol (25 ml) was added triethylamine (0.72 ml, 5.2 mmol) and the solution heated at 50° C. for two days. The solution was evaporated under reduced pressure and purified by chromatography (dichloromethane:ethyl acetate 1:1 then CHCl$_3$/MeOH 2%) to give 2 products. Product 1 was identified as the 5-membered cyclised product (0.57 g, 54%). Compound 2 was identified as the desired product (7.4), (0.39 g, 37%). $δ_H$(DMSO-d6) 2.36, 2.38 (6H, 2×s, 2×ArCH3), 2.43–57 (4H, m, H2', H2", C5-CH$_2$), 3.45 (2H, t, J 7.6 Hz, N—CH$_2$), 3.93 (2H, d, J4.7 Hz, CH$_2$Ph), 4.43–4.63 (3H, m, H4', H5', H5"), 5.54–5.57 (1H, m, H3'), 5.67 (1H, t, J4.7 Hz, NH), 6.36 (1H, t, J6.7 Hz, is H1'), 6.63 (1H, d, J7.7 Hz, Ph-H6), 6.75–6.78 (2H, m, Ph-H2, Ph-H4), 7.09 (1H, t, J 7.7 Hz, Ph-H5), 7.30–7.37 (5H, m, 4×ArCH, H6), 7.85–7.92 (4H, m, ArCH), 9.34 (1H, s, OH) ppm.

EXAMPLE 8
Synthesis of 1 and 2-(6'-(fluorescein-5-carboxamidohexanoyl))-6-(2'-deoxy-β-D-ribofuranosyl)-3,4-dihydro-8H-pyrimido[4,5-c][1,2] pyridazin-7-one-5'-triphosphate (8.5)
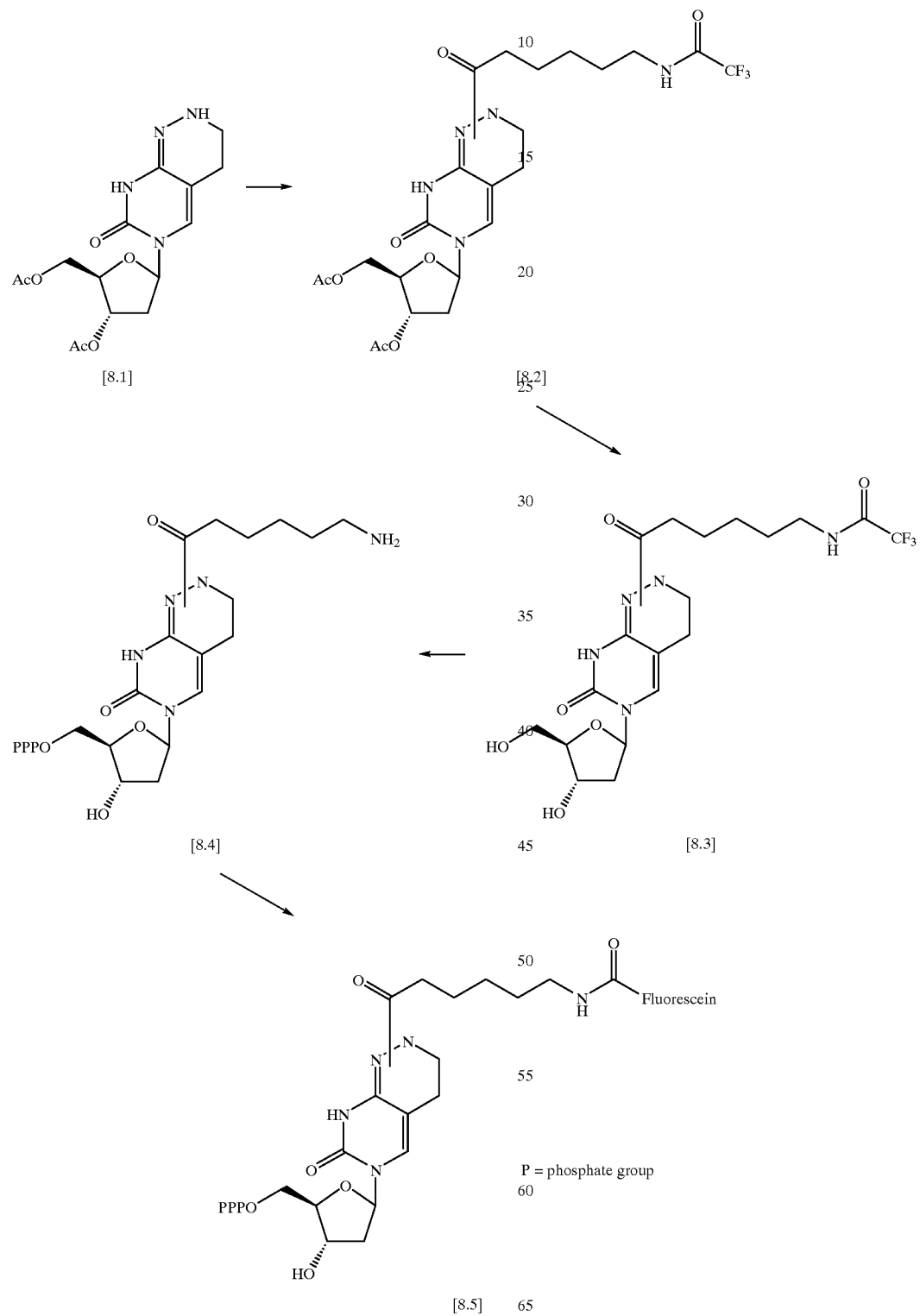
P = phosphate group

Preparation of 6-(3,5-diacetyl-2-deoxy-β-D-ribofuranosyl)-3,4-dihydro-8H-pyrimido[4,5-c][1,2]pyridazin-7-one (8.1)

1-(3,5-Di-O-acetyl-2-deoxyribofuranosyl)4-(1,2,4-triazolo)-5-(2-chloroethyl)pyrimido-2-one (P. Kong Thoo Lin and D. M. Brown, *Nucleic Acids Res.* 17, 10373–10383, 1989) (0.25 g, 0.6 mmol) was dissolved in dry dichloromethane (10 ml) and anhydrous hydrazine (37 μl, 1.2 mmol) added and the solution stirred at room temperature for 30 minutes. The solution was concentrated and purified by chromatography (chloroform/1 0% methanol) to give the title compound (8.1) as a white solid. Yield 0.2 g, 100%.

$\delta_H$ (DMSO-d6) 1.96, 2.01 (6H, 2×s, 2×CH$_3$CO), 2.15–2.45(2H, m, H2', H2"), 2.75(2H, t, J 6.8 Hz, CH$_2$), 3.6(1H, br, s, NH), 3.83(2H, t, J6.8 Hz, CH$_2$N), 4.12–4.14 (1H, m, H4'), 4.21 4.24(2H, m, H5', H5"), 5.17–5.20(1H, m, H3'), 6.18(1H, t, J6.2 Hz, H1'), 7.17(1H, s, H6), 9.72(1H, s, NH) ppm. m/z 352 M+. Accurate mass measurement found 352.1376 (C$_{15}$H$_{20}$N$_4$O$_6$) deviation −0.7 ppm. UV λmax 279.6 (ε=14800).

Preparation of 1 and 2-(6-(trifluoroacetamido)hexanoyl)-6-(3',5'-diacetyl-2'-deoxy-β-D-ribofuranosyl)-3,4-dihydro-8H-pyrimido[4,5-c][1,2]pyridazin-7-one (8.2)

To a stirred solution of the 3',5'-diacetyl nucleoside (8.1) (350 mg, 1 mmol) in anhydrous dichloromethane (25 ml) was added the N-hydroxysuccinimidyl ester of N-(trifluoroacetyl)-6-aminohexanoic acid (356 mg, 1.1 mmol) and triethylamine (110 mg, 1.1 mmol) and the mixture was stirred at room temperature for 4 hours. The solution was then concentrated to dryness and thin-layer chromatography of the reaction mixture in 5% methanol/chloroform indicated the presence of two minor and one major product. The major product was purified by column chromatography to give a white solid compound though the positional isomer cannot be specified from the data available.

$\delta_H$(CDCl$_3$) 1.27–1.79 (6H, m, 3×CH$_2$), 2.10, 2.14 (6H, 2×s, 2×COCH$_3$), 2.12, 2.41 (2H, m, H2', H2"), 2.73 (2H, t, J6.8 Hz, NCOCH$_2$), 3.22–3.47 (3H, m, CH$_2$N), 3.70 (2H, t, J6.8 Hz, C5-CH$_2$), 4.14–4.43 (3H, H5',H5", H3'), 5.11–5.25 (1H,m,H4'),6.24 (1H, t, J6.6 Hz, H1'), 7.31 (1H, s, H6) 9.56, 11.38 (2×s, NH) ppm.

Preparation of 1 and 2-(6-(trifluoroacetamido)hexanoyl)-6-(2'-deoxy-β-D-ribofuranosyl)-3,4-dihydro-8H-pyrimido[4,5-c][1,2]pyridazin-7-one (8.3)

The 3',5'-diacetyl nucleoside containing the N-trifluoroacetyihexanoyl linker (8.2) (500 mg, 0.9 mmol) was dissolved in methanol (20 ml) and to the stirring solution, at room temperature, was added a methanolic solution of sodium methoxide (2.0 ml, 0.5M, 1.0 mmol). After 20 minutes, the solution was evaporated under reduced pressure and the product chromatographed on a silica gel column (CHCl$_3$/10% methanol) to give the title compound (8.3) (250 mg, 56%) as a white solid.

$\delta_H$ (DMSO-d6)1.27–1.52 (6H, m, 3×CH$_2$), 1.84–2.50 (2H, m, H2', H2"), 2.18 (2H, t, J6.8 Hz, NCOCH$_2$), 2.85 (2H, m, CH$_2$N), 3.19 (1H, m, CHN), 3,39 (1H, m, CHN), 3.52 (2H, m, C5-CH$_2$), 3.70–3.81 (3H, m, H5', H5",H3'), 3.394.01 (1H, m, H4'), 6.18 ( 1H, t, J 6.6 Hz, H1'), 7.71 (1H, s, H6), 9.43,10.22 (2×s NH) ppm.

Preparation of 1 and 2-(6-aminohexanoyl)-6-(2'-deoxy-β-D-ribofuranosyl)-3,4-dihydro-8H-pyrimido[4,5-c][1,2]pyridazin-7-one-5'-triphosphate ( 8.4)

To a stirred and cooled (0° C.) solution of 2-(6-(trifluoroacetamido)hexanoyl)-6-(2'-deoxy-β-D-furanosyl)-3,4-dihydro-8H-pyrimido[4,5-c][1,2]pyridazin-7-one (8.3) (220 mg, 0.46 mmol) in trimethylphosphate (2 ml) was added POCl$_3$ (65 μl. 0.69 mmol). After one hour, the reaction mixture was simultaneously treated with 0.5M DMF solution of bis-n-tributylammonium pyrophosphate (4.72 ml, 2.30 mmol) and n-tributylamine (547 ml, 2.30 mmol). After stirring the reaction mixture at room temperature for 10 minutes, it was neutralised with 1.0M TEAB (triethylammonium bicarbonate) and stirred at room temperature overnight, evaporated under reduced pressure and the residue obtained was dissolved in water (30 ml). Thus, the crude triphosphate was loaded on a Sephadex column (500 ml) and the desired triphosphate eluted using the gradient 0.05 (2L) to 1.0M TEAB (2L, pH=7) at 2 ml/min flow rate. After characterising it by $^{31}$P nmr, $\delta_p$ (D$_2$O/EDTA) −10.36 (d, γ-P), −10.86 (d, (α-P), −22.79 (t, β-P) ppm, the triphosphate was treated with 30% NH$_4$OH (6 ml) overnight for the deprotection of the amino group. The reaction mixture was evaporated under reduced pressure and the residue obtained was purified by semi-prep-HPLC using Waters Delta Pak 15 micron C18 column (5cm×30cm) under the gradient conditions of 0–00% buffer A (0.1 M TEAB) and buffer B (25% CH$_3$CN in 0.1M TEAB) at 130 ml/min over 30 minutes. The desired triphosphate (8.4) fractions were pooled, evaporated and lyophilised to get pure (8.4) (83 mg, 19.45%) as the triethylammonium salt.

Preparation of 1 and 2-(6'-(fluorescein-5-carboxamidohexanoyl)) -6-(2'-deoxy-β-D-ribofuranosyl)-3,4-dihydro-8H-pyrimido[4,5-c][1,2]pyridazin-7-one-5'-triphosphate (8.5)

To a stirred solution of the triphosphate (8.4) (5 mg, 0.05 mmol) in 0.2M Na$_2$CO$_3$-NaHCO$_3$ buffer (800 μpH 8.5) was added an anhydrous DMF solution (600 μl) of the N-hydroxysuccinimidyl ester of 5-carboxyfluorescein (10 mg, 0.02 mmol) at room temperature and stirring continued overnight. After evaporating the reaction mixture under reduced pressure, the yellow coloured residue obtained was dissolved in a minimum amount of 1:1 aqueous methanol, loaded on a glass column (40 cm×2 cm) packed up to 20 cm height with 35–70 microns silica gel 60 (EM-Separations, cat no. 9389-5). The excess dye was eluted using 1:1 chloroform/methanol to neat methanol and the desired nucleotide-fluorescein conjugate was eluted using 6:3:1 i-PrOH:NH$_4$OH:H$_2$O to obtain (8.4) as a yellow solid after pooling and evaporation. Compound (8.5) was further purified by HPLC on a 15 microns Delta Pak C18 column (1.9 cm×30 cm) under the gradient conditions of 0–50% buffer A (0.1 M TEAB, pH 7.1) and buffer B (25% acetonitrile in 0.1M TEAB, pH 7.0) at 15 ml per minute in 30 minutes. The desired compound (8.5) fractions were pooled, evaporated and lyophilised to get pure (8.5) as a yellow solid (quantitative yield).

EXAMPLE 9

Synthesis of Nucleoside Triphosphates

All the following triphosphates were prepared in an analogous manner to the triphosphate example (8.4)

6-(2-Deoxy-β-D-ribofuranosyl)-3,4-dihydro-3(R,S)-methyl-8H-pyrimido[4,5-c][1,2]oxazin-7-one-5'-triphosphate (9.1)

Derived from nucleoside (2.4)

$\delta_P$(121 MHz;D$_2$O) −10.91 (d, γ-P), −11.51 (d, α-P) and −23.33 (t, β-P)

6-(2-Deoxy-β-D-ribofuranosyl)-3,4-dihydro-3(R,S)-but-5-enyl-8H-pyrimido[4,5c][1,2]oxazin-7-one-5'-triphosphate (9.2)

Derived from nucleoside (4.4)

$\delta_H$(300MHz; D$_2$O/KOH) 1.65 (2H, m, allyl), 2.0–2.8 (6H, m), 3.65 (1H, m, sugar). 4.0 (3H, m, sugar+H3), 4.5 (1H, broad, sugar). 4.9 (2H, dd, allyl), 5.75 (1H, m, allyl), 6.2 (1H, m, sugar), 7.0 (1H, s) ppm.

$\delta_P$(121 MHz:D$_2$O/KOH) −5.84 (d, γ-P), −11.00 (d, α-P) and −21.88 (t, β-P)

6-(2-Deoxy-β-D-ribofuranosyl)-3,4-dihydro-3(R,S)-(N(2,4-dinitrophenyacyl)-3-aminopropyl)-8H-pyrimido[4,5-c][1,2]oxazin-7-one-5'-triphosphate (9.3)

Derived from nucleoside (3.6)

$\delta_H$(300 MHz; D$_2$O) 2.0–2.4 (3H, m), 2.6–3.0 (4H, m), 3.8 (1H, m, sugar), 4.0 (3H, m, sugar+H3), 4.45 (1H, m), 6.15 (1H, m, sugar), 7.1 (1H, 2×s) ppm $\delta_P$(121 MHz; D$_2$O/H$_2$O) −10.83 (d, γ-P), -11.46 (d, α-P) and −23.19(t, β-P)

EXAMPLE 10

Synthesis of tritiated 6-(2-deoxy-β-D-ribofuranosyl)-324-dihydro-3(R,S)-butyl-8H-pyrimido[4,5c][1,2]oxazin-7-one (10.1)

A solution of 6-(2-deoxy-β-D-ribofuranosyl)-3,4-dihydro-3(R,S)-but-5-enyl-8H-pyrimido[4,c][1,2]oxazin-7-one 5'-triphosphate (22 mg) in methanol (1.5 ml) was stirred with 10%Pd/C (4 mg) and tritium gas (5Ci) for 20 minutes, after which time 1 Ci of tritium gas had been consumed. The catalyst was filtered off using a Milex-SR filter, and labile tritium was removed by repeated evaporations from methanol. The final residue was dissolved in methanol (20 ml). The yield was 648 mCi. One ml of the above solution was taken to dryness and dissolved in 10 mM aqueous tris buffer pH8 to give a radioactive concentration of of 8 mCi/ml.

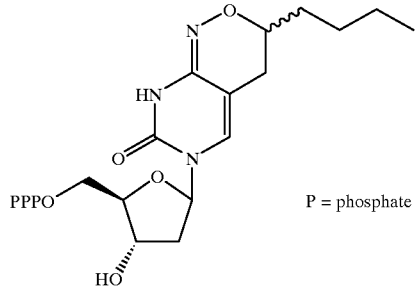

[10.1]

P = phosphate

EXAMPLE 11

Primer Extension Assay

In order to test whether the analogue triphosphates were accepted by exo minus Klenow polymerase as substrates, primer extension reactions were carried out with the following templates:
a) 3' ACGTACACGACCTCTACCTTGCTA 5'
b) 3' ACGTACACGACCTCTGAACTAGTC 5'

Primer complementary to the sequence underlined was 5' end labelled with [γ$^{33}$P] ATP and T4 polynucleotide kinase. Reactions were boiled for 5 minutes after labelling to remove any PNK activity.

For each extension reaction, 1 picomole of $^{33}$P 5'end-labelled primer was hybridised with 2 pmole of template in 10 μl ×2 Klenow buffer. The primer and template solution was heated at 75° C. for 3 minutes, then allowed to cool slowly to 30° C. over at least 30 minutes. The solution was diluted twice by the addition of 5U exonuclease minus Klenow enzyme (Amersham), 2 mU inorganic pyrophosphatase (Amersham) with 40 μM analogue nucleoside triphosphate and/or 4 μM TTPαS or 250 μM dATP and dGTP. Reactions were incubated at 37° C. for 30 minutes, then stopped by the addition of formamide stop solution. Reaction products were separated on a 19% polyacrylamide 7M urea gel and sized by comparison with a $^{33}$p labelled 8 to 32 base oligonucleotide ladder after exposure to Biomax autoradiography film or a phosphor screen (Storm phosphorimager, Molecular Dynamics).

Usng the first template, single base extension was seen as expected with TTP; controls in the absence of added 17P showed no extension. Similarly, the triphosphates of the methyl P analogue (2.4), the butenyl P analogue (4.4), the dinitrophenol-labelled P analogue (3.6), the benzyl hydrazino P analogue (7.3) and the tritiated analogue (10.1) were lo efficiently incorporated. This is in agreement with published observations that the triphosphate of nucleoside analogue P (dPTP) is a good substrate for Taq DNA polymerase.

Using the second template, single base extension was seen as expected with dCTP; controls in the absence of added dCTP showed no extension. Similarly, the triphosphate of the methyl P analogue (2.4), the butenyl P analogue (4.4) and the dinitrophenol-labelled analogue (3.6) were efficiently incorporated. Addition of both purines allowe the extension of the primer to full length products in the presence of the analogue and the added pyrimidine.

EXAMPLE 12

Oligonucleotide Tailing with Terminal Deoxynucleotidyl Transferase

In order to test the ability of the analogue triphosphates to be accepted by terminal deoxynucleotidyl transferase as a substrate, an oligonucleotide tailing reaction was performed.

A 15 mer primer (sequence: 5' TGC ATG TGC TGG AGA 3') and 8 to 32 base oligonucleotide markers were 5' end labelled with [γ33p] ATP and T4 polynucleotide kinase. Reactions were boiled for 5 minutes after labelling to remove any PNK activity. Four picomoles of the labelled primer, 25 U terminal deoxynucleotidyl transferase and 32 μM dNTP or analogue triphosphate were incubated in 25 μl 1 00mM cacodylate buffer pH7.2, 2 mM CoCl$_2$ and 0.2 mM 2-mercaptoethanol for 90 minutes at 37° C. The reactions were stopped by the addition of formamide stop solution and the reaction products run on a 19% polyacrylamide 7M urea gel with the labelled markers. Autoradiography using Biomax film was carried out on the dry gel.

The results showed that of the native bases, dATP and TTP produced the longest tails, followed by dCTP and then dGTP. While dPTP itself was the best of the analogue substrates for TdT, appearing to incorporate at least as well as dATP based on migration of the product on the gel, the triphosphate of the 3-methyl analogue of P (compound 2.4) was also a good substrate, the tailing products running between those produced using dATP or TTP and dCTP. The triphosphates of 3-butenyl-P (4.4) and benzyl hydrazino P (7.3) were also substrates though the products were rather small.

In a separate experiment, it was shown that both the fluorescein-labelled compound (8.5) and the amidocaproate-labelled compound (8.4) produced tails, the tails being of length 16 to 20 bases and 4 to 5 bases respectively.

EXAMPLE 13

Detection of DNA by Means of Antibodies Directed Against P Base

Antibodies were raised against P base so that DNA containing P could be detected. In order to conjugate P base to a protein carrier it was necessary to add a linker and functional group at the 1 position (which is normally occupied by a sugar in the nucleoside).

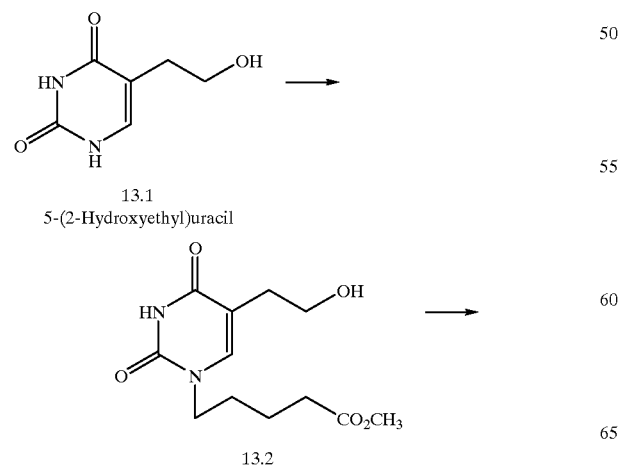

13.1
5-(2-Hydroxyethyl)uracil

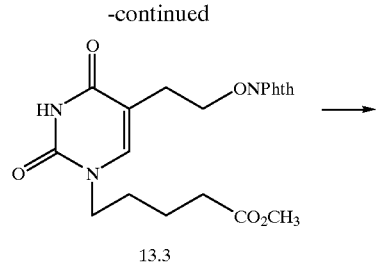

13.3

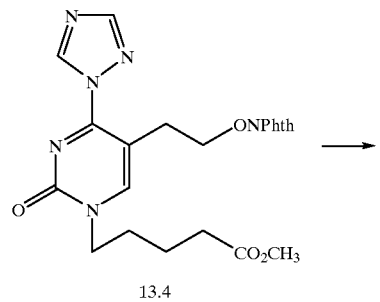

13.4

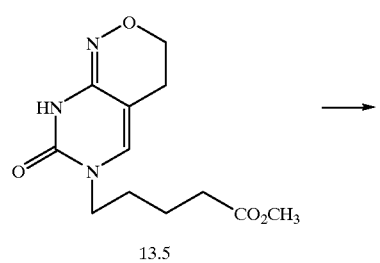

13.5

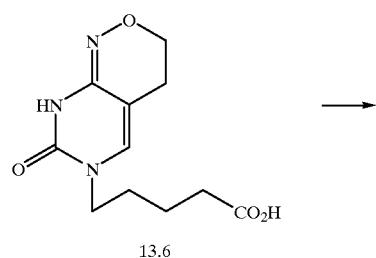

13.6

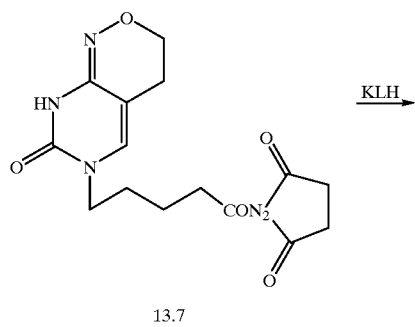

13.7

-continued

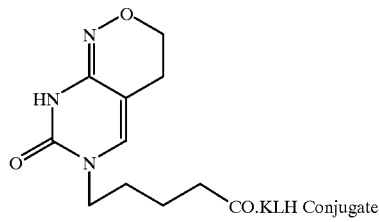

13.8

Synthesis of 1-(4-carboxybutyl)-3,4-dihydro-8H-pyrimido-[4,5-c][1,2]oxazine-7-one

Preparation of 5-(2-hydroxyethyl)uracil (13.1)

5-(2-Hydroxyethyl)uracil was prepared following the method of Lin and Brown, Methods in Molecular Biology vol.26, pages 187 to 206 (1994), ed. S. Agrawal, Humana Press Inc.

Preparation of 1-(4-methylcarboxybutyl)-5-(2-hydroxyethyl)uracil(13.2)

5-(2-Hydroxyethyl)uracil (13.1) (5.38 g, 19.9 mmol) was suspended in 1,1,1,3,3,3-hexamethyldisilazane (27 ml) and chlorotrimethylsilane (4 ml) under a nitrogen atmosphere. The mixture was refluxed for 2 hours. The reaction mixture was cooled to ambient temperature and then reduced to a yellow oil by rotary evaporation. The oil was redissolved in anhydrous toluene (5 ml) and again reduced to an oil.

The oil was dissolved in anhydrous acetonitrile (20 ml) and methyl-5-bromovalerate (13 ml, 91 mmol) was added. This reaction was heated at reflux under an atmosphere of argon for 18 hours. The mixture was then cooled and reduced to an oil by rotary evaporation. The product was purified by liquid chromatography on silica gel eluting with a stepped gradient of chloroform and methanol. The product was isolated and recrystallized from petroleum ether to yield 1-(4-methylcarboxybutyl)-5-(2-hydroxyethyl)uracil (13.2) (6.63 g, 71.2%), MP 105° C. The structure was confirmed by mass spectroscopy and proton NMR.

Preparation of 1-(4-methylcarboxybutyl)-5-(2-phthalimido-oxyethyl)uracil (13.3)

1-(4-Methylcarboxybutyl)-5-(2-hydroxyethyl)uracil (13.2) no (6.213 g. 23 mmol) was dissolved in anhydrous tetrahydrofuran. N-Hydroxyphthalimide (7.505 g, 46 mmol) and triphenylphosphine (12.046 g, 46 mmol) were added and the solution stirred at ambient temperature. Diethylazodicarboxylate (9.95 g, 57 mmol) was added in 0.5 ml aliquots over 10 minutes, the reaction was then stirred for a further hour. The product was recrystallized twice from chloroform : diethyl ether mixtures to yield 1-(4-methylcarboxybutyl)-5-(2-phthalimidooxyethyl)uracil (13.3) (8.77 g, 91.8%). The structure was confirmed by mass spectroscopy and proton NMR.

Preparation of 1-(4-methylcarboxybutyl)-5-(2-phthalimido-oxyethyl)4-triazolopyrimidine (13.4)

1,2,4-Triazole (11.843 g, 171 mmol) was dissolved in anhydrous acetonitrile (200 ml) and stirred at 0° C. Phosphorus oxychloride (3.9 ml, 42 mmol) was added dropwise followed by triethylamine (31 ml, 225 mmol). Stirring was continued at 0C for 1 hour. 1-(4-Methylcarboxybutyl)-5-(2-phthalimido-oxyethyl)uracil (3) (4.16 g, 10 mmol) dissolved in anhydrous tetrahydrofuran (50 ml) and anhydrous acetonitrile (80 ml) was added slowly to the above stirred solution. The mixture was heated at 50° C. for 2.5 hours and then cooled to 0° C. to yield a white precipitate. The product was further purified by column chromatography on silica gel, eluting with chloroform : acetone (7:3). This produced 1-(4-methylcarboxybutyl)-5-(2-phthalimido-oxyethyl)-4-triazolouracil (13.4) as an oil (3.43 g, 73.4%). The structure was confirmed by mass spectroscopy and proton NMR.

Preparation of 1-(4-methylcarboxybutyl)-3,4-dihydro-8H-pyrimido [4,5-c][1,2]oxazine-7-one (13.5)

1-(4-Methylcarboxybutyl)-5-(2-phthalimido-oxyethyl)-4-triazolopyrimidine (4) (0.49 g, 1.05 mmol) was dissolved in anhydrous 3) dioxan (30 ml). Anhydrous dioxan saturated with ammonia (70 ml) was added and the reaction mixture was stirred for 24 hours. The product was purified by thin-layer chromatography on silica gel GF plate eluted with chloroform : ethanol (95:5) (0.21 g, 74.9%). The structure was confirmed by mass spectroscopy.

Preparation of 1-(4-carboxybutyl)-3,4-dihydro-8H-pyrimido[4,5-c][1,2]oxazine-7-one, ammonium salt (13.6)

1-(4-Methylcarboxybutyl)-3,4-dihydro-8H-pyrimido[4,5-c][1,2]oxazine-7-one (13.5) (0.42 g, 1.57 mmol) was dissolved in 1M aqueous sodium hydroxide solution (10 ml) and stirred for 2 hours. The mixture was applied to an ion exchange column of Dowex 50 WX8-200. This was eluted with water and the product recovered using 2M aqueous ammonia solution. The solution volume was reduced and then freeze-dried to yield a white solid (0.24 g, 60.4%). The product appeared as a single spot when analysed in the following thin-layer chromatography systems: Silica gel eluted with chloroform:methanol (7:3) and butan-1-ol: water, glacial acetic acid (12:5:3); Silica gel impregnated with ODS eluted with methanol:water:glacial acetic acid (80:20:1); Cellulose eluted with butan-1-ol:water:glacial acetic acid (12:5:3). The structure was confirmed by mass spectroscopy and proton NMR.

Preparation of P base KLH conjugate (13.8)

1-(4-Carboxybutyl)-3,4-dihydro-8H-pyrimido[4,5-c][1,2]oxazine-7-one (6) (41.6 mg, 0.164 mmol) was dissolved in dimethylsulphoxide (2 ml). N-Hydroxysuccinimide (26.5 mg, 0.23 mmol) and 1-ethyl-3-(3-dimethylaminopropyl) carbodiimide (65.4 mg, 0.341 mmol) were added and the mixture was stirred at ambient temperature for 26 hours. The dimethylsulphoxide was removed under vacuum. The residue was purified by column chromatography on silica gel and eluting with acetone.

The product (13.7) was isolated by removing the solvent by rotary evaporation.

The N-succinimidyl ester (13.7) was dissolved in DMF (1 ml) and the KLH suspension (90 mg protein) dissolved in pyridine (0.5 ml) and water (4.5 ml) was added. The mixture was stirred under an atmosphere of nitrogen for 4 hours. The product was dialysed with water for 5 days. The conjugate (13.8) was isolated by freeze-drying to yield 59 mg. This was submitted to Polyclonal Antibodies Ltd for antiserum production.

Antiserum Production

Three sheep were immunised with the KLH conjugate. The primary immunisation was carried out with the conjugate formulated in Freunds complete adjuvant. Subsequent reimmunisations were carried out with the conjugate formulated in Freunds incomplete adjuvant at 4 weekly intervals. Blood samples were taken 2 weeks after each reimmunisation and serum prepared.

Testing of Antisera

Antisera were tested against dot blots of P-labelled oligonucleotides ( i.e. P itself being the label) on nylon membrane using a second antibody conjugated to horseradish peroxidase with ECL substrate for detection. The response of pre-immune serum taken from each animal was compared with serum taken from the first and second bleeds.

One microlitre aliquots containing 10, 5, 1, 0.5, 0.1, 0.05 and 0.01 pmole of P-labelled oligonucleotide (sequence: 5' PPP GTC ACG AC 3') diluted in water were dotted onto Hybond N+ membrane. A one microlitre aliquot of control oligonucleotide (sequence: 5' TGC TGG AGA 3') diluted in water was also applied. Blots prepared in this way were baked at 80° C. for 90 minutes to fix the DNA. After baking, a one microlitre aliquot of a 1:1000 dilution of pre-immune serum was dotted onto each blot to give a positive control.

The blots were incubated for 60 minutes at room temperature with shaking in Liquid Block (Amersham) diluted 1:10 with 10 mM phosphate buffered saline (PBS). Individual blots were then incubated for 60 minutes with shaking in 1:1000, 1:10000 or 1:50000 dilutions of each serum sample in 0.5% bovine serum albumin (BSA) solution in PBS. They were then washed 3 times for 10 minutes each wash with shaking in PBS containing 0.3% Tween 20. The blots were then incubated for 60 minutes with shaking in horseradish-peroxidase conjugated affinity-purified donkey anti-sheep IgG, H+L (Jackson ImmunoResearch Labs Inc) diluted 1:25000 in 0.5% BSA in PBS, then washed three times for 10 minutes each wash with shaking in PBS containing 0.3% Tween 20. They were then incubated in ECL detection reagent (Amersham) for 1 to 2 minutes and then exposed to Biomax film (Amersham) for 2 minutes and 5 minutes.

Positive signals were seen from antisera obtained after immunisation of all three sheep at all dilutions. A maximum sensitivity of 0.1 picomole P-labelled oligonucleotide was obtained with the 1:1000 antiserum dilution. Some background signal was seen with the unlabelled oligonucleotide at the 1:1000 dilution of all the serum samples, including the preimmune serum, but this was not seen at the 1:10000 or 1:50000 dilutions. A strong signal was obtained from the positive control.

This experiment demonstrates the potential for detecting or capturing oligonucleotide or other probes tailed or otherwise labelled with nucleotide analogues.

EXAMPLE 14

Detection of M13 on Dot Blots wing 3'end labelled probes

Oligonucleotide probes labelled with fluorescein- or dinitrophenol-containing nucleotide analogues were detected after hybridisation to target DNA immobilised on a membrane.

Probe Preparation

Six microlitres (12 picomoles) −40 forward sequencing primer 23 mer (sequence 5'GTTTTCCCAGTCACGACG1TGTA-3') was mixed with 10 $\mu$l×5 reaction buffer 500 mM sodium cacodylate pH 7.2, 10 mM $CoCl_2$, 1 mM 2-mercaptoethanol), 50 units terminal deoxynucleotidyl transferase, 15 $\mu$l 800 $\mu$M fluorescein labelled compound (8.5) or the dinitrophenol labelled compound (9.3) and water added to give a final volume of 50 $\mu$l. Both reactions were incubated at 37° C. for 90 minutes. The reactions were then boiled for 5 minutes to remove any remaining terminal deoxynucleotidyl transferase activity.

Blot Preparation

Dot blots of M13 single-stranded DNA were prepared on Hybond N+ membrane. Eight dots were applied to each membrane containing 1200, 240, 120, 48, 36, 24, 12 and 6 picograms corresponding to 500, 100, 50, 20, 15, 10, 5 and 2.5 attomoles of target respectively. The dots were fixed to the membrane by baking in an oven at 80° C. for 90 minutes.

Hybridisation Method

Duplicate dot blots were pre-hybridised in 5 mi hybridisation buffer (0.5% dextran sulphate, 0.1% sodium dodecyl sulphate (SDS), 1:20 liquid block (Amersham Life Science) and x5 sodium chloride sodium citrate buffer (SSC)) for 30 minutes at 42° C. Twenty-five microlitres (~50 ng) of the probes prepared above was added to each hybridisation to give a probe concentration of 10 ng/ml. The blots were placed in a 42° C. shaking waterbath for 60 minutes.

The blots were then washed in 5 ml×5 SSC/0.1% SDS at room temperature for 5 minutes. This wash was repeated with a further 5 ml×SSC/0.1% SDS at room temperature for 5 minutes.

The blots were then washed in 5 ml×l SSC/0.1% SDS at 42° C. for 15 minutes. This wash was repeated with a further 5 ml×1 SSC/0.1% SDS at 42° C. for 15 minutes.

The blots were then transferred to 1:10 dilution of liquid block, Amersham, diluted in TBS buffer (0.3M sodium chloride 0.1M Trizma base pH 7.5) and placed on an orbital shaker for 30 minutes.

For the detection of DNP-containing probes, blots were transferred to 5 ml 0.5% w/v BSA in TBS buffer pH 7.5. To this was added 5 $\mu$l anti-DNP horseradish peroxidase conjugated antibody (giving a 1:1000 dilution of the antibody).

For the detection of fluorescein-containing probes blots were transferred to 5 ml 0.5% w/v BSA in TBS buffer pH 9.5. To this was added 5 $\mu$l anti-fluorescein alkaline phosphatase conjugated antibody (gives a 1:1000 dilution of the antibody).

Both sets of blots were them transferred to an orbital shaker for 45 minutes.

The blots were drained and transferred to either 25 ml 0.1% vv Tween-20 in TBS pH 7.5 (DNP-labelled probe) or 25 ml 0.1% v/v Tween-20 TBS pH 9.5 (fluorescein-labelled probe) and placed on the orbital shaker for 15 minutes. This wash step was repeated, three times in total, with a further 5 ml 0.1% v/v Tween-20 TBS buffer at the relevant pH.

Detection of alkaline phosphatase (fluorescein-labelled probe)

The blots were drained and transferred to Saran Wrap. 0.5 ml CDP-Star™ reagent was applied to each blot and left at room temperature for 5 minutes. The blots were drained then wrapped in Saran Wrap and exposed to autoradiography film for 30 minutes. On the developed film it was possible to see all the dots from the 500 to the 2.5 attomole dot.

Detection of Horseradish Peroxidase (DNP-Labelled Probe)

The blots were drained and transferred to Saran Wrap. A 0.5 ml aliquot of ECL detection reagent (Amersham) (made by mixing solution 1 and 2 in equal amounts) was applied to each blot and left at room temperature for 2 minutes. The blots were drained then wrapped in Saran Wrap and exposed to autoradiography film for 10 minutes. On the developed film it was possible to see the 500 and 100 attomole dots. Greater sensitivity can be obtained by optimisation of the antibody concentration to reduce background.

What is claimed is:

1. A nucleoside analogue of the formula

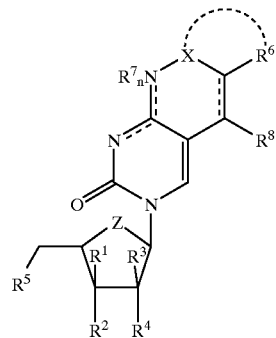

wherein X is O, S, Se, SO, CO or N—$R^{10}$, the dotted line represents an optional link between $R^6$ and $R^{10}$, $R^1$, $R^2$, $R^3$ and $R^4$ are the same or different and each is H, OH, F, $NH_2$, $N_3$, O-hydrocarbyl, or a reporter moiety, $R^5$ is OH or mono-, di- or tri-phosphate or -thiophosphate or corresponding boranophosphate, or one of $R^2$ and $R^5$ is selected from the group consisting of a phosphoramidite, H-phosphonate, methylphosphonate, and phosphorothioate for incorporation in a polynucleotide chain, Z is O, or S, and $R^6$, $R^7$, $R^8$, $R^9$ and R are the same or different and each is H or alkyl or aryl or a reporter moiety, n is 0 or 1, provided that at least one reporter moiety is present on a member selected from the group consisting of $R^1$ to $R^4$ and $R^6$ to $R^{10}$, wherein a reporter moiety comprises a linker group, together with a signal moiety or a solid surface, or a reactive group for attachment of a signal moiety or a solid surface to the nucleoside analogue.

2. A nucleoside analogue as claimed in claim 1, wherein X is O and Z is O.

3. A nucleoside analogue as claimed in claim 1, wherein $R^5$ is triphosphate.

4. A nucleoside analogue as claimed in claim 1, wherein $R^6$ or $R^{10}$ comprises a reporter moiety.

5. A nucleoside analogue as claimed in claim 1, wherein the reporter moiety comprises a signal moiety and a linker group.

6. A nucleoside analogue as claimed in claim 1, wherein the linker group is a chain of up to 30 carbon, nitrogen, oxygen and sulphur atoms, rigid or flexible, unsaturated or saturated.

7. A nucleoside analogue as claimed in claim 1, wherein the reactive group is $NH_2$, OH, COOH, $CONH_2$, or SH.

8. A polynucleotide chain comprising at least one residue of a nucleoside analogue according to claim 1.

9. A nucleoside analogue as claimed in claim 8, wherein one of $R^2$ and $R^5$ is phosphoramidite or H-phosphonate.

10. A polynucleotide chain as claimed in claim 8, wherein a signal moiety has been introduced into the incorporated nucleoside analogue residue.

11. A method of detecting a nucleic acid which contains a residue of a nucleoside analogue of the formula

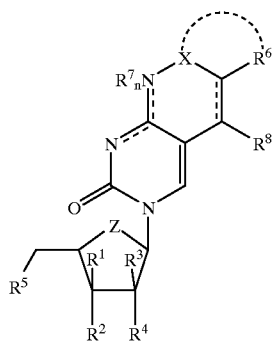

wherein X is O, S, Se, SO, CO or N—$R^{10}$, the dotted line represents an optional link between $R^6$ and $R^{10}$, $R^1$, $R^2$, $R^3$ and $R^4$ are the same or different and each is H, OH, F, $NH_2$, $N_3$, O-hydrocarbyl, or a reporter moiety, $R^5$ is OH or mono-, di- or tri-phosphate or -thiophosphate or corresponding boranophosphate, or one of $R^2$ and $R^5$ is a phosphoramidite or other group for incorporation in a polynucleotide chain, Z is O, or S, and $R^6$, $R^7$, $R^8$, $R^9$ and $R^{10}$ are the same or different and each is H or alkyl or aryl or a reporter moiety, n is 0 or 1, which method comprises the steps of:

(a) combining said nucleic acid with an antibody which binds to said analogue; and (b) detecting the presence of said nucleic acid.

* * * * *

UNITED STATES PATENT AND TRADEMARK OFFICE
CERTIFICATE OF CORRECTION

PATENT NO. : 6,313,286 B1
DATED : November 6, 2001
INVENTOR(S) : Brown et al.

It is certified that error appears in the above-identified patent and that said Letters Patent is hereby corrected as shown below:

Column 43,
Line 36, delete the comma between "0" and "or 5"
Line 37, replace "R" with -- $R^{10}$ --

Column 44,
Line 45, delete the comma between "0" and "or 5"

Signed and Sealed this

Fourth Day of June, 2002

Attest:

JAMES E. ROGAN
Attesting Officer   Director of the United States Patent and Trademark Office